US012168126B2

(12) United States Patent
Hendricks

(10) Patent No.: US 12,168,126 B2
(45) Date of Patent: Dec. 17, 2024

(54) SYSTEMS AND METHODS FOR A CONFORMABLE MODULAR ELECTRODE FOR APPLICATION OF AN ALTERNATING ELECTRIC FIELD TO TISSUE

(71) Applicant: Dignity Health, San Francisco, CA (US)

(72) Inventor: Benjamin Hendricks, San Francisco, CA (US)

(73) Assignee: Dignity Health, San Francisco, CA (US)

(*) Notice: Subject to any disclaimer, the term of this patent is extended or adjusted under 35 U.S.C. 154(b) by 0 days.

(21) Appl. No.: 18/551,453

(22) PCT Filed: Apr. 4, 2022

(86) PCT No.: PCT/US2022/023321
§ 371 (c)(1),
(2) Date: Sep. 20, 2023

(87) PCT Pub. No.: WO2022/216614
PCT Pub. Date: Oct. 13, 2022

(65) Prior Publication Data
US 2024/0173546 A1    May 30, 2024

Related U.S. Application Data

(60) Provisional application No. 63/170,514, filed on Apr. 4, 2021.

(51) Int. Cl.
*A61N 1/36* (2006.01)
*A61N 1/02* (2006.01)
*A61N 1/04* (2006.01)

(52) U.S. Cl.
CPC ......... *A61N 1/36002* (2017.08); *A61N 1/025* (2013.01); *A61N 1/0476* (2013.01); *A61N 1/36031* (2017.08); *A61N 1/36034* (2017.08)

(58) Field of Classification Search
CPC .. A61N 1/36002; A61N 1/025; A61N 1/0476; A61N 1/36031; A61N 1/36034
See application file for complete search history.

(56) References Cited

U.S. PATENT DOCUMENTS

| | | | |
|---|---|---|---|
| 8,244,377 B1* | 8/2012 | Pianca | A61N 1/0573 607/116 |
| 10,285,646 B1* | 5/2019 | Grant | A61B 5/7221 |

(Continued)

OTHER PUBLICATIONS

Patent Cooperation Treaty, International Search Report and Written Opinion, International Application No. PCT/US2022/023321, date of mailing Jul. 12, 2022, 10 pages.

*Primary Examiner* — Mallika D Fairchild
(74) *Attorney, Agent, or Firm* — Polsinelli PC

(57) ABSTRACT

A modular electrode system for therapeutic application of an electric field to a tissue is described. The modular electrode system includes a flexible scaffold that conforms to a variable convex or concave surface such as a resected tissue cavity or other target tissue area and includes one or more surface electrodes in addition to one or more depth electrodes. The modular electrode system includes a control system that communicates with the plurality of electrodes of the flexible scaffold to deliver a stimulating voltage and receive measured voltage values for real-time optimization of the electric field generated within the tissue.

27 Claims, 24 Drawing Sheets

(56) References Cited

U.S. PATENT DOCUMENTS

| | | | |
|---|---|---|---|
| 2006/0085056 A1* | 4/2006 | Schouenborg | A61N 1/0502 |
| | | | 607/148 |
| 2008/0027509 A1 | 1/2008 | Andino et al. | |
| 2010/0004715 A1* | 1/2010 | Fahey | A61B 5/313 |
| | | | 607/152 |
| 2011/0118655 A1* | 5/2011 | Fassih | A61N 1/205 |
| | | | 604/20 |
| 2013/0144365 A1* | 6/2013 | Kipke | A61B 5/4064 |
| | | | 607/148 |
| 2017/0361091 A1* | 12/2017 | Tai | A61N 1/04 |
| 2020/0069213 A1* | 3/2020 | Salo | A61N 1/048 |

* cited by examiner

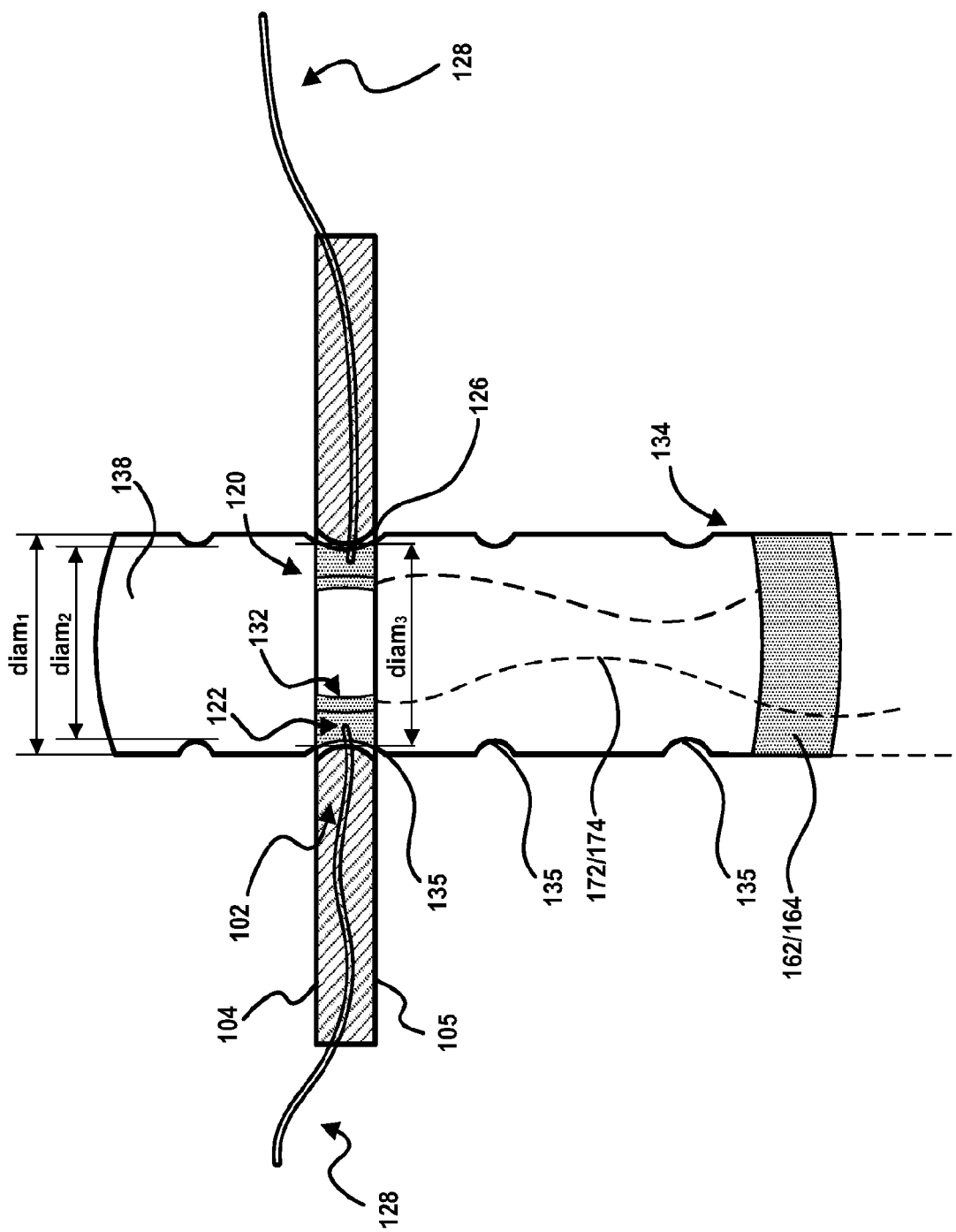

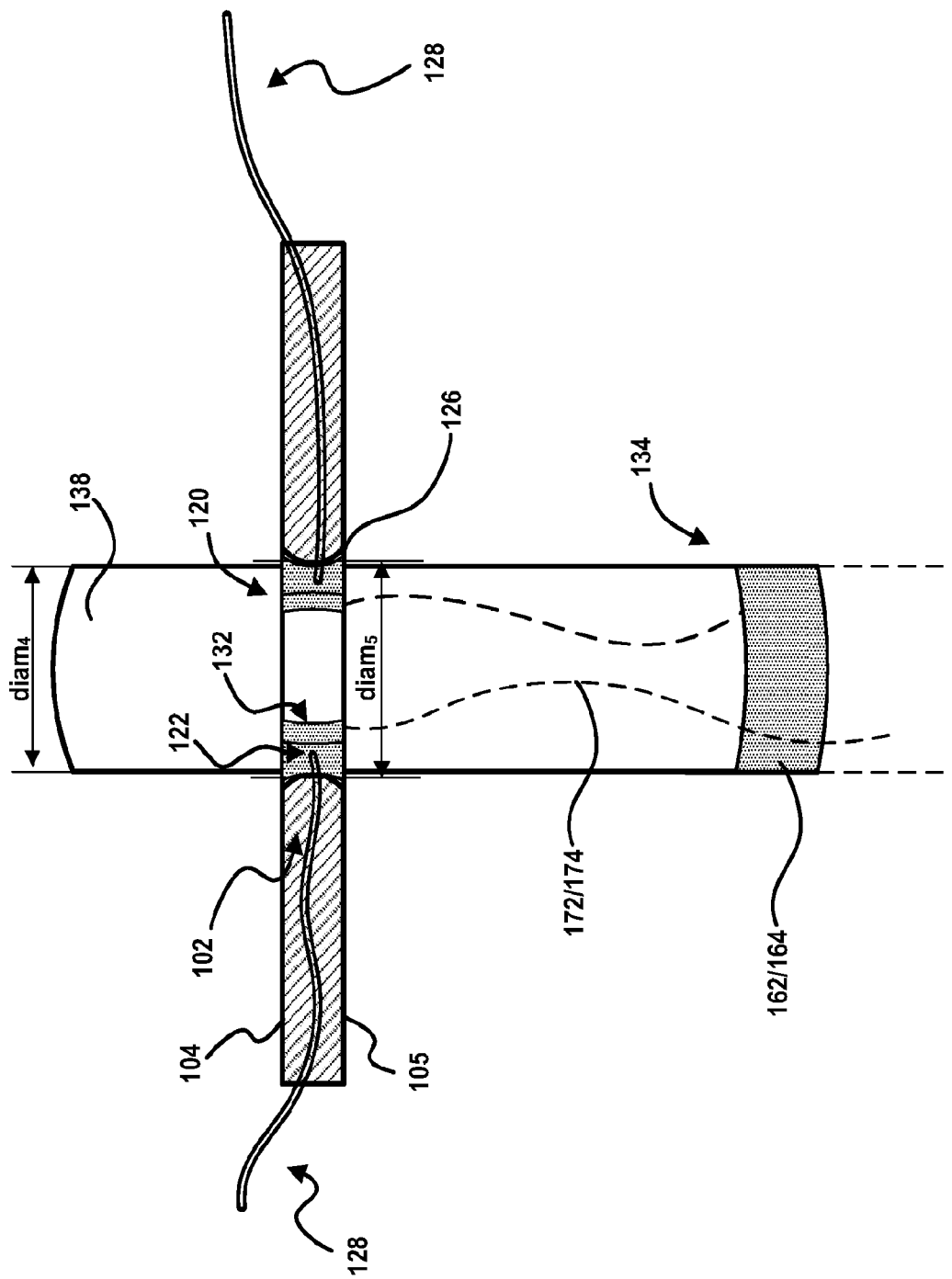

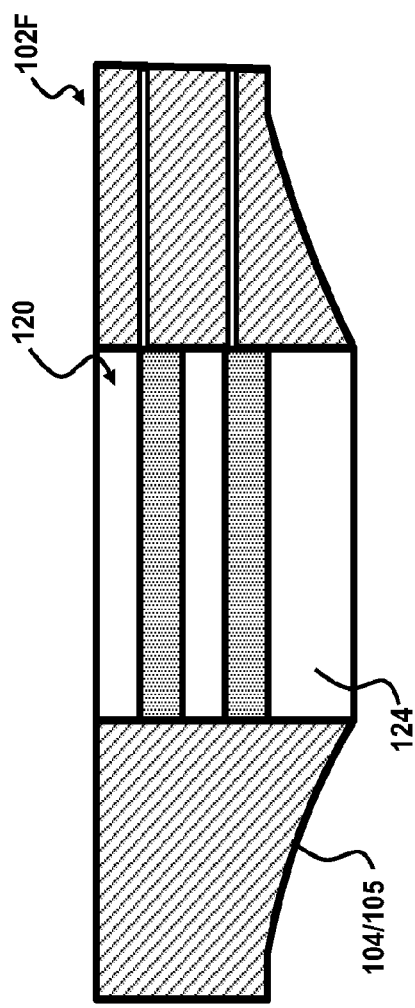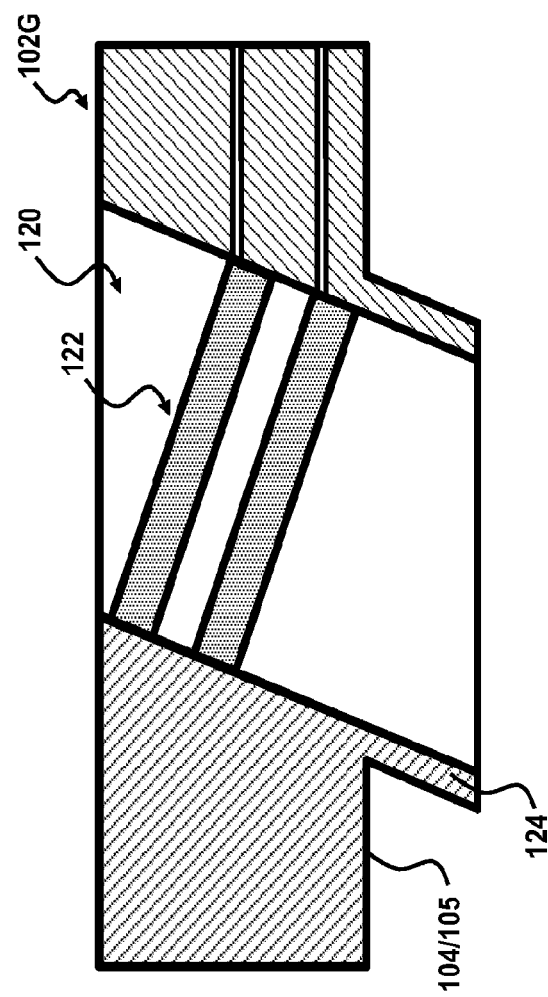

SYSTEMS AND METHODS FOR A CONFORMABLE MODULAR ELECTRODE FOR APPLICATION OF AN ALTERNATING ELECTRIC FIELD TO TISSUE

CROSS-REFERENCE TO RELATED APPLICATIONS

This is a PCT application that claims benefit to U.S. Provisional Patent Application Ser. No. 63/170,514 filed Apr. 4, 2021, which is herein incorporated by reference in its entirety.

FIELD

The present disclosure generally relates to therapeutic application of alternating electric field to tissue, and in particular, to a system and associated method for a conformable modular electrode for therapeutic application of alternating electric field to tissue.

BACKGROUND

For patients that undergo a surgical resection of a tumor and still experience recurrent tumors, a vast majority of recurrent tumors will occur within the margin of the previous surgical resection even if a complete tumor resection was achieved. Therefore, implantation strategies for electric field-based treatment of tumors that undergo surgical resection should be on tissue immediately adjacent to the removed tissue. Given that a magnitude of electric field is maximized at regions where there is a dramatic change in voltage, it is ideal to apply a stimulating voltage directly adjacent to tumor cells or remaining tissue that is otherwise in danger of experiencing tumor recurrence. However, existing electrode systems often fail to achieve optimal placement within the body.

It is with these observations in mind, among others, that various aspects of the present disclosure were conceived and developed.

BRIEF DESCRIPTION OF THE DRAWINGS

FIGS. 7A-7C are cross-sectional views showing the depth electrode of FIG. 6 inserted into the depth electrode port;

FIGS. 10A and 10B are a series of illustration showing alternative depth electrode ports of FIG. 4B;

Corresponding reference characters indicate corresponding elements among the view of the drawings. The headings used in the figures do not limit the scope of the claims.

DETAILED DESCRIPTION

Various embodiments of a modular electrode system for therapeutic application of an electric field to a target tissue area are described herein. In particular, the modular electrode system defines a flexible scaffold that conforms to a variable convex or concave surface such as a resected tissue cavity or other target tissue area. The modular electrode system further includes a plurality of electrodes disposed along a planar body of the flexible scaffold; the plurality of electrodes can include one or more surface electrodes in addition to one or more depth electrodes which are configured for insertion through the flexible scaffold at variable depth into the target tissue area. The flexible scaffold can include one or more perforations to allow flexibility and conformity and can also be cut to a desired shape or size depending on the specific needs of the surgical case. Further, the modular electrode system includes a control system that communicates with the plurality of electrodes of the flexible scaffold to deliver a stimulating voltage and receive measured voltage values for real-time optimization of the electric field being delivered.

Figure 1:
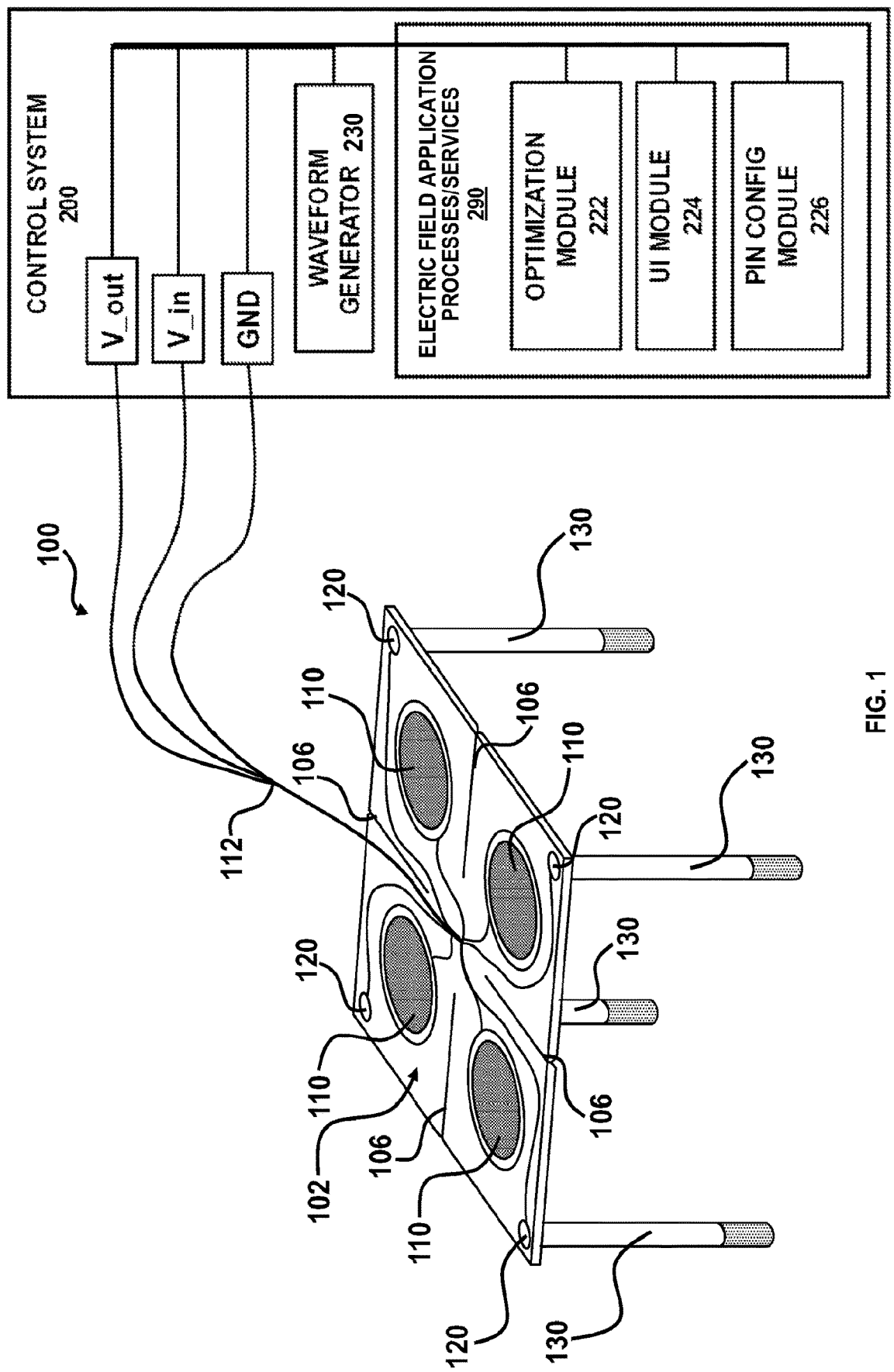
FIG. 1 is an illustration showing a modular electrode in electrical communication with a control system application of a therapeutic electric field.
Figure 2:
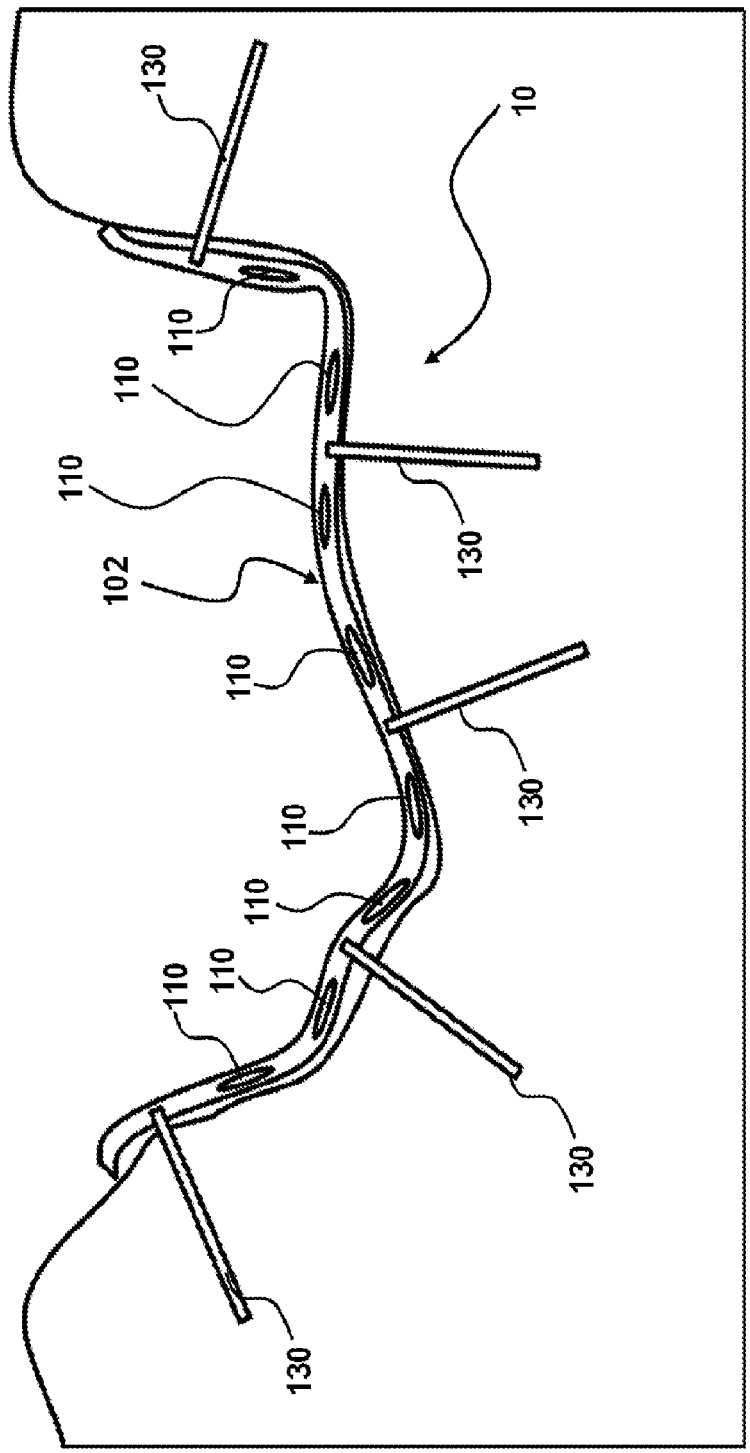
FIG. 2 is an illustration showing the modular electrode of FIG. 1 engaged with a target tissue area for application of a therapeutic electric field.

Referring to FIGS. 1 and 2, the modular electrode 100 includes a flexible scaffold 102 that conforms to a target tissue area 10. In a primary embodiment, the flexible scaffold 102 includes a plurality of surface electrodes 110 and additionally provides a structure for one or more depth electrodes 130 configured for insertion into the adjacent target tissue area 10 for applying a customizable therapeutic electric field to the target tissue area 10. The target tissue area 10 can be a resected tissue area, or "tumor bed", and can also be placed to treat a tumor in situ (i.e., without a resection). The modular electrode 100 permits control of both electric field strength and orientation by a control system 200 in electrical communication with the modular electrode 100. The control system 200 provides power to various components of the modular electrode 100, measures resultant electric field strength or voltage values, and interprets measurement results to optimize the applied electric field.

Flexible Scaffold

Figure 3:
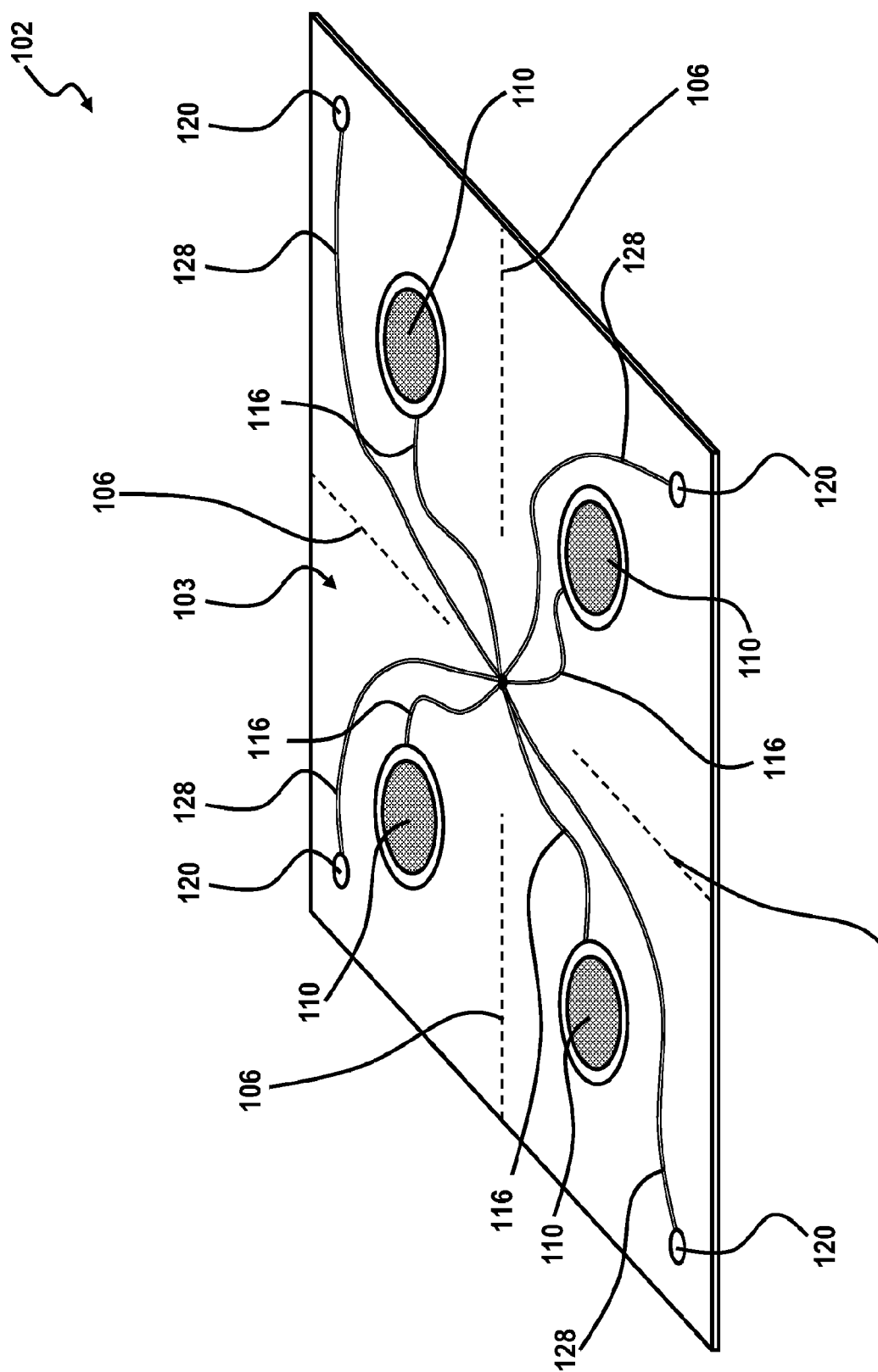
FIG. 3 is a top perspective view showing a flexible scaffold of the modular electrode of FIG. 1.
Figure 4A:
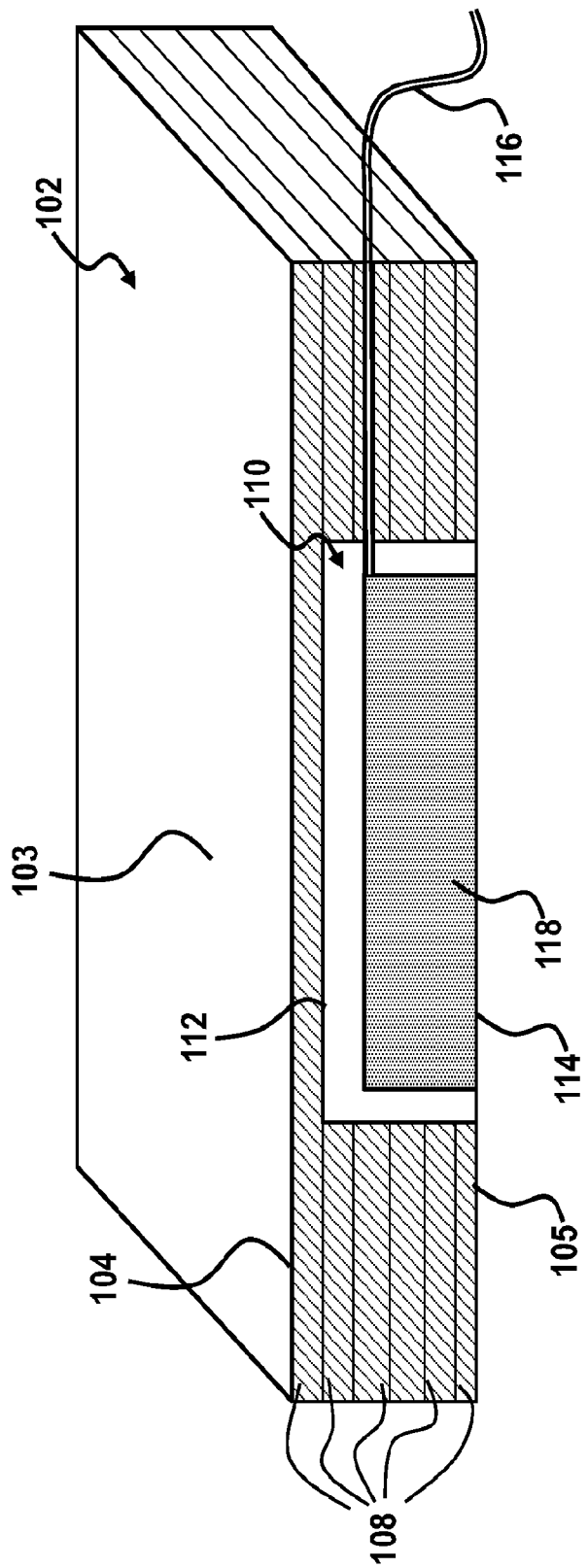
FIG. 4A is a cross-sectional view showing a surface electrode embedded within the flexible scaffold of FIG. 3.
Figure 4B:
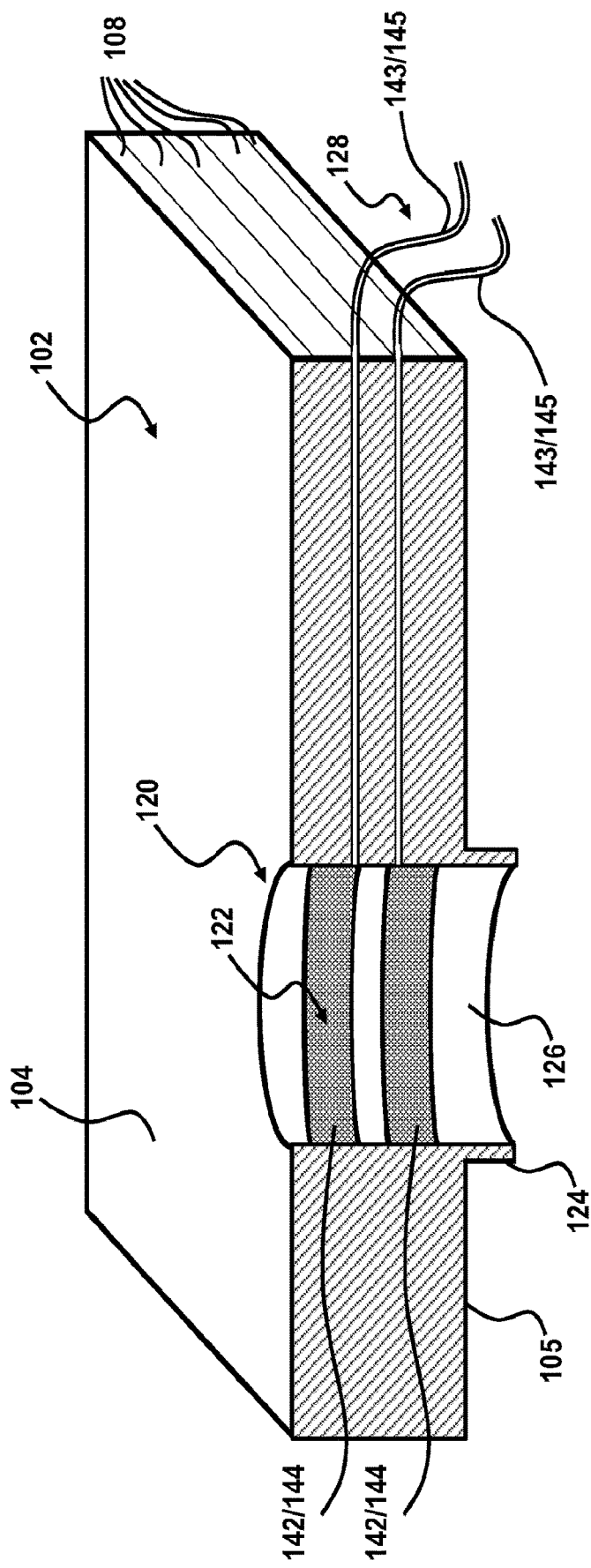
FIG. 4B is a cross-sectional view showing a depth electrode port embedded within the flexible scaffold of FIG. 3.
Figure 4C:
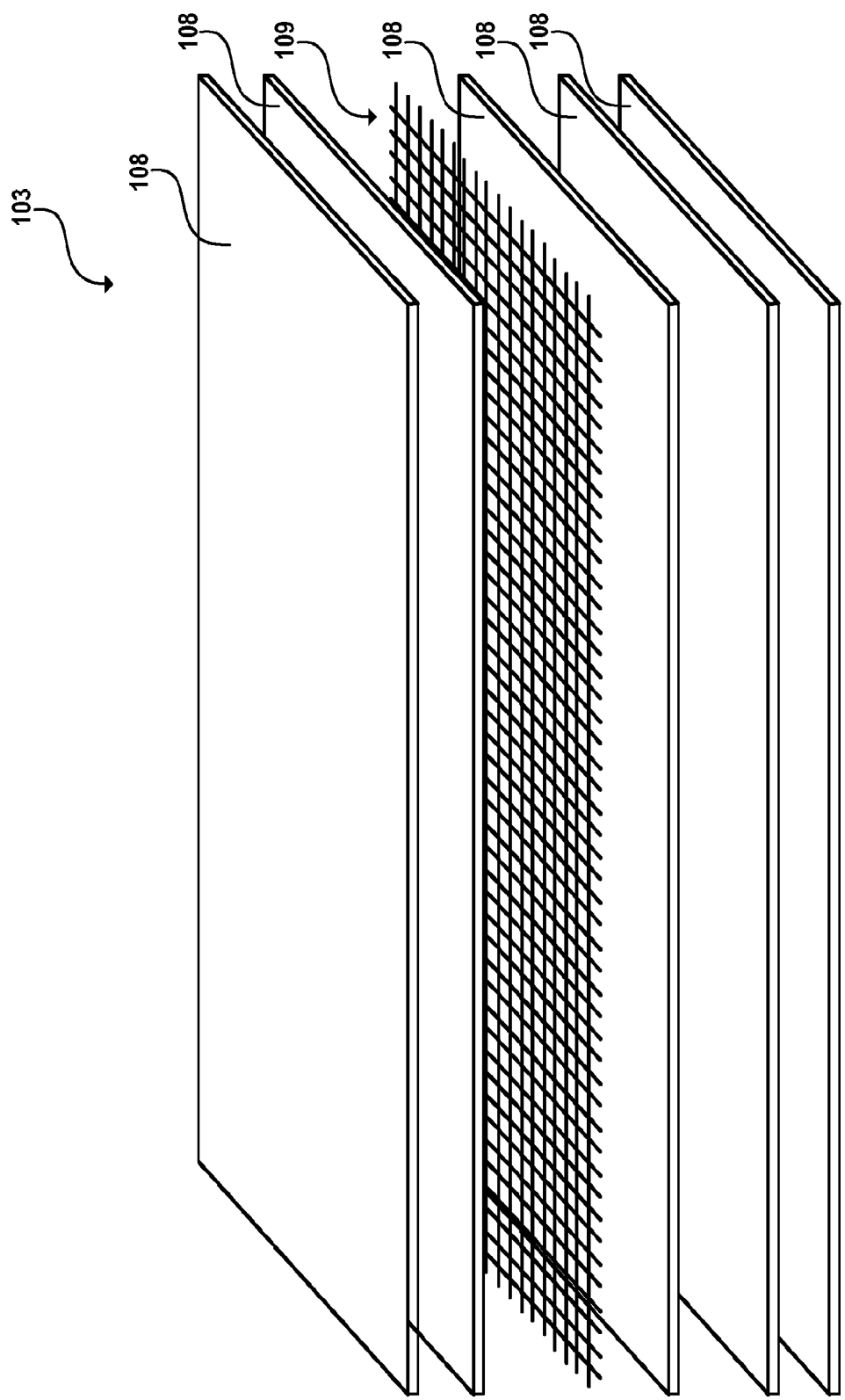
FIG. 4C is an exploded view showing various layers and a mesh structure of the flexible scaffold of FIG. 3.

FIGS. 3-4C illustrate the flexible scaffold 102 which defines a planar body 103 defining a first surface 104 and an opposite second surface 105 (FIGS. 10A and 10B). The flexible scaffold 102 can include one or more layers 108 of silicon or another similar inert polymer material that at least partially encapsulates the plurality of surface electrodes 110 and associated electrical connections. As shown in FIG. 4C, the flexible scaffold 102 can include a mesh structure 109 between layers 108 which provides some degree of rigidity and strength to the flexible scaffold 102. The flexible scaffold 102 can be formed using a large silicone-based quadrangular mold (or other applicable configuration, as will be discussed in greater detail below) with in-laid surface electrodes 110. The mesh structure 109 can be a netting-like structure made of nylon or another suitable material placed between the layers 108 the flexible scaffold, or can optionally be intermixed throughout the material of the flexible scaffold 102 (i.e. not as a separate layer but some combination of nylon fibers or particles mixed within the silicon material) to add some rigidity to the structure. The flexible scaffold 102 can include one or more perforations 106 (alternatively characterized as gaps or slits) to enable flexible conformity to a target tissue area such as target tissue area 10 of FIG. 2. As shown, the flexible scaffold 102 maintains electrical connections for the plurality of surface electrodes 110 and for the depth electrode 130 in electrical communication with a control system 200 that provides power to the plurality of surface electrodes 110 and/or the depth electrode 130. In the example of FIG. 4A, a surface contact wire 116 associated with a surface electrode 110 is encapsulated between layers 108 (FIG. 4B) of the flexible scaffold 102.

Referring directly to FIG. 4B, the flexible scaffold 102 additionally includes one or more depth electrode ports 120 for insertion of one or more respective depth electrodes 130. Each depth electrode port 120 defines a "thru-hole" 126 through which a depth electrode 130 can be disposed at variable or fixed depth into the target tissue area to apply an electric field within the tissue. In some embodiments, the depth electrode port 120 defines a directing tube 124 that guides an orientation of the depth electrode 130 when the depth electrode 130 is disposed through the depth electrode port 120. The directing tube 124 can extend below the first surface 104 or the opposite second surface 105 of the flexible scaffold 102 towards the surface of the target tissue area, depending on which first surface 104 or second surface 105 is interfacing with the surface of the target tissue area. Alternatively, referring briefly to FIG. 10A, the first surface 104 or the opposite second surface 105 of the flexible scaffold 102 can taper gently around the directing tube 124 such that the directing tube 124 does not extend beyond the first surface 104 or the opposite second surface 105. As shown in FIG. 10B, an orientation of the directing tube 124 relative to the flexible scaffold 102 can vary between 0 and 90 degrees. In some embodiments, the directing tube 124 can be rigid.

The directing tube 124 of the depth electrode port 120 can include one or more port contacts 122 defined along a length of directing tube 124 to transmit power and measured voltage between the depth electrode 130 and the control system 200. In some embodiments, the one or more port contacts 122 can be ring-shaped, but can also be in the form of other shapes such as strips defined along a direction of elongation of the directing tube 124 or thru-hole 126 such as in the embodiment of FIGS. 7B and 7C. In the illustrated embodiment of FIG. 4B, each respective port contact 122 of the one or more port contacts 122 can fluidly assume a role of stimulating port contact 142 or measuring port contact 144, based on a pin configuration provided by the control system 200. Further, each respective port contact 122 is associated with one or more port wires 128 which are encapsulated between layers 108 of the flexible scaffold 102. Port wires 128 can include one or more stimulating port wires 143 or measuring port wires 145, based on the assigned roles of each respective associated port contact 122 as dictated by the control system 200. The depth electrode port 120 can couple the associated depth electrode 130 to the flexible scaffold 102 at a fixed depth or can optionally couple the depth electrode 130 to the flexible scaffold 102 at a variable depth.

The flexible scaffold 102 can be manufactured in multiple varieties to feature a single surface electrode 110, a single depth electrode 130 and associated depth electrode port 120, multiple surface electrodes 110, multiple depth electrodes 130 and associated depth electrode ports 120, and/or a combination of surface electrodes 110 and depth electrodes 130 in varying quantity and intra-contact and inter-contact distances, as shown in FIGS. 9A-9G and as will be discussed in greater detail below. In some embodiments, the flexible scaffold 102 is wired in such a way that enables a practitioner to cut the flexible scaffold 102 to a desired shape and size; this may involve disconnecting one or more surface electrodes 110 and/or depth electrode ports 120 while still enabling one or more remaining surface electrodes 110 and/or depth electrode ports 120 to function.

Optionally, the flexible scaffold 102 can be without perforations to maintain a more rigid structure. For a flexible scaffold 102 without perforations, a multilayered polymer construction or differing polymer composition can be adopted.

Materials for the construction of the flexible scaffold 102 can be non-absorbable by the body or can otherwise be dissolvable and absorbable by the body. For a non-absorbable flexible scaffold 102, contemplated materials include silicone (polymer is basis of flexible scaffold 102) and nylon as the mesh structure 109 within silica. For an absorbable flexible scaffold 102, materials can include a stereocopolymer of poly-(L-lactide-co-D, L-lactide) (PDLLA) 70:30, or can alternatively use stereocopolymer of poly-L-DL-lactic acid (PLDLLA).

Surface Electrodes

Referring to FIGS. 1-4A and 5, the plurality of surface electrodes 110 can be mounted directly to the flexible scaffold 102 with associated surface contact wires 116 being encapsulated by one or more layers 108 of the flexible scaffold 102. As shown in FIG. 4A, surface electrodes 110 can each include a first face 112, an opposite second face 114, and a surface contact 118 that directly applies voltage to tissue or receives resultant voltage within the tissue for measurement. The plurality of surface electrodes 110 can form a grid pattern along the planar body 103 of the flexible scaffold 102, the grid featuring at least one surface electrode 110 but including as many surface electrodes 110 as necessary. In some embodiments, the grid can feature up to one hundred individual surface electrodes 110; however, it should be noted that any number of surface electrodes 110 are contemplated, given the modularity of modular electrode 100. The plurality of surface electrodes 110 can be located along the first surface 104 and/or the second surface 105 of the flexible scaffold 102 to interface directly with the target tissue area 10 and for application of the electric field, as shown in FIGS. 2 and 4A. The plurality of surface electrodes 110 can be of variable size to deliver across variable surface areas, depending on the location of the target tissue area 10. The plurality of surface electrodes 110 can individually associate with the control system 200 for individual control of each surface electrodes 110 of the plurality of surface electrodes 110. In a further embodiment, the surface electrodes 110 can be configured for applying voltage to the target tissue area 10 or can optionally be configured for measuring the resultant voltage within the target tissue area 10. As such, the flexible scaffold 102 can include a combination of surface electrodes 110 that are individually assigned to "stimulating" or "measuring" roles.

Depth Electrodes

Figure 6:
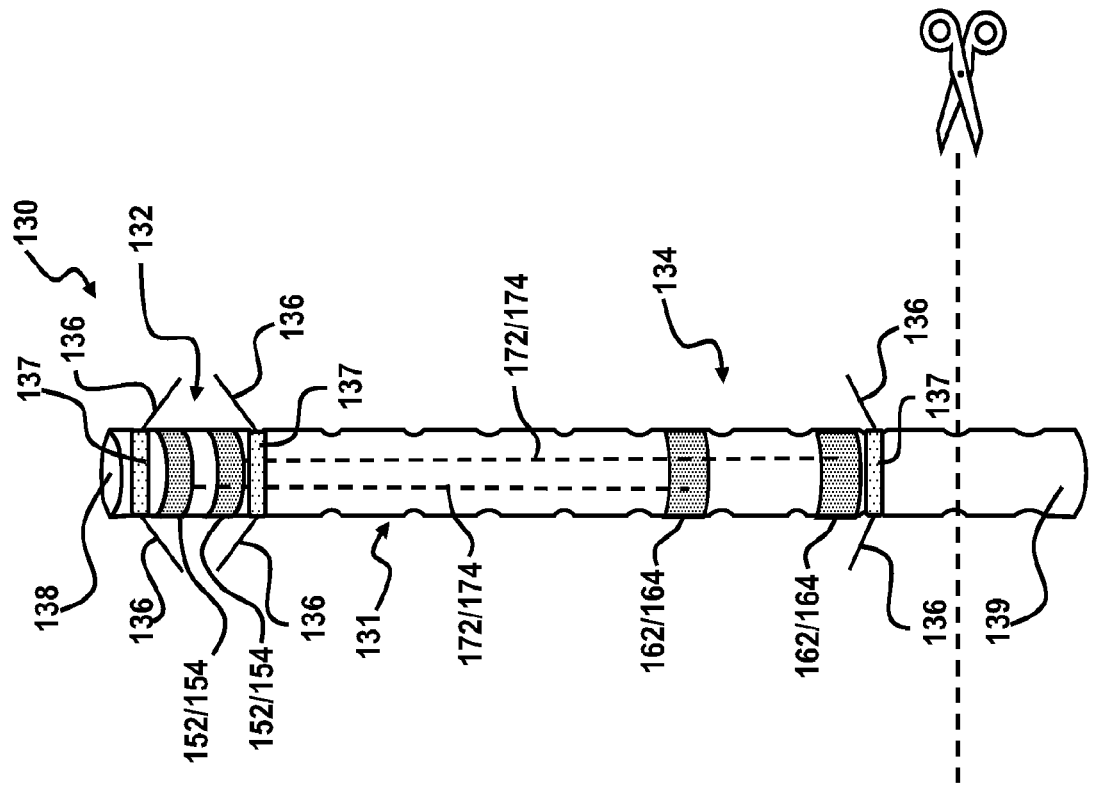
FIG. 6 is a perspective view showing a depth electrode of the modular electrode of FIG. 1.
Figure 5:
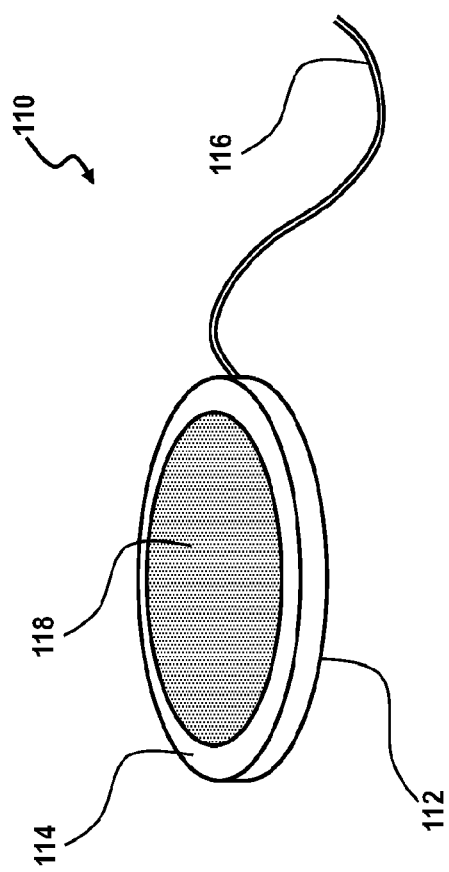
FIG. 5 is a perspective view showing a surface electrode of the modular electrode of FIG. 1.

Referring to FIGS. 6-8B, the one or more depth electrodes 130 defines an elongated electrode body 131 having a proximal portion 138 and an opposite distal portion 139. The proximal portion 138 of the elongated electrode body 131 is configured to interface with a respective depth electrode port 120 of the one or more depth electrode ports 120, as specifically illustrated in FIGS. 7A-7C, and includes one or more interfacing contacts 132 for electrical communication with the control system 200. In particular, the one or more interfacing contacts 132 interface directly with the one or more port contacts 122 of an associated depth electrode port 120. FIG. 7A shows the one or more one or more interfacing contacts 132 embodied as ring around the elongated electrode body 131, and FIG. 7B shows the one or more one or more interfacing contacts 132 and strips defined along a direction of elongation of the electrode body 131. The distal portion 139 of the elongated electrode body 131 is interfaces directly with the target tissue area 10 (FIG. 2) and defines one or more terminal contacts 134 in electrical communication with the one or more interfacing contacts 132. In the example of FIG. 6, the one or more interfacing contacts 132 can fluidly assume the role of a measuring interfacing contact 154 or a stimulating interfacing contact 152, and the one or more terminal contacts 134 can fluidly assume the role of a measuring terminal contact 164 or a stimulating terminal contact 162 based on assigned roles provided by the control system 200. In a primary embodiment, the one or more depth electrodes 130 can be trimmed to size by the practitioner and then disposed within an associated depth electrode port 120 at variable depth to interface with the port contact 122.

The stimulating interfacing contact 152 of a depth electrode 130 can couple with a stimulating port contact 142 of the port contact 122 of the depth electrode port 120 to apply a stimulating voltage from the control system 200 to the target tissue area at the associated stimulating terminal contact 164. Similarly, the measuring interfacing contact 154 of a depth electrode 130 can couple with a measuring port contact 144 of the port contact 122 of the depth electrode port 120 to receive a measured voltage from the target tissue area as measured at the associated measuring terminal contact 164 and communicate the measured voltage to the control system 200. As shown, the depth electrode 130 includes electrical connections 172/174 between each respective stimulating/measuring interfacing contact 152/154 and each respective stimulating/measuring terminal contact 162/164. In some embodiments, multiple stimulating terminal contacts 162 and measuring terminal contacts 164 can be present along a single depth electrode 130. It should be noted that individual interfacing contacts 132 and terminal contacts 134 can be fluid in their assigned roles; in particular, the control system 200 can assign or re-assign stimulating and measuring interfacing and terminal contacts 152/154 and 162/164 as needed.

Additionally, the one or more depth electrodes 130 permit pairing with one or more respective surface electrodes 110 to optimize the applied electric field through measurement of voltage within the target tissue by the one or more depth electrodes 130 and subsequent adjustment of parameters by the control system 200 that apply voltage to the target tissue through surface electrodes 110.

Figure 7A:
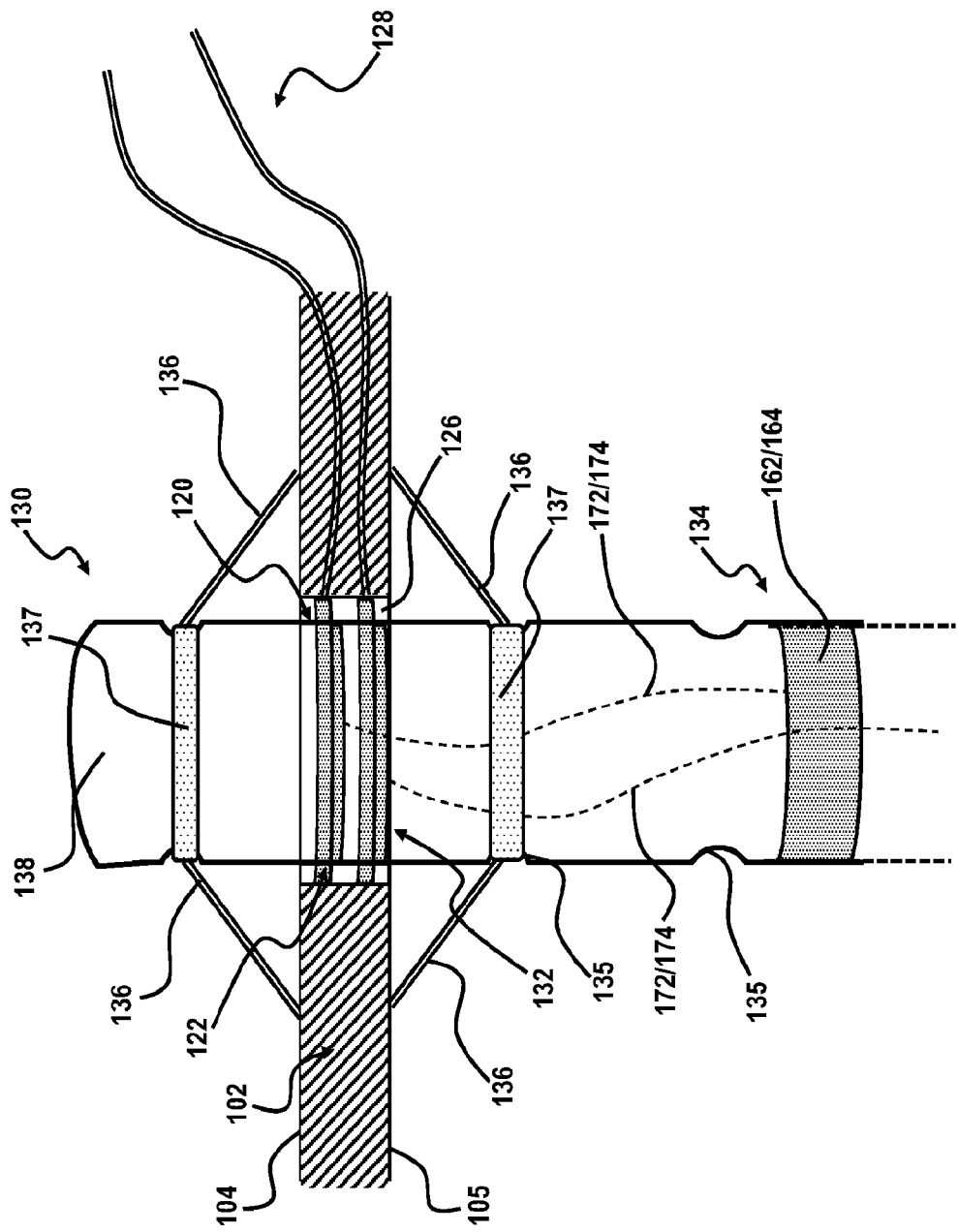

The one or more depth electrodes 130 can additionally provide structural support to anchor the modular electrode 100 at the target tissue area. In particular, the one or more depth electrodes 130 can include a plurality of tines 136 that anchor the depth electrode 130 within tissue below the target tissue area and prevent unintentional extraction of the depth electrode 130 from the flexible scaffold 102. The plurality of tines 136 can be located at multiple locations along the length of the depth electrode 130; in the embodiment of FIGS. 6-7B, a depth electrode 130 includes one or more divots 135 defined along the elongated electrode body 131 that provide locations for placement of the plurality of tines 136, as in the case of FIG. 7A. As shown, the plurality of tines 136 can include one or more tine rings 137 that allow variable placement of the plurality of tines 136 along the length of the elongated electrode body 131. However, FIG. 7B illustrates an embodiment of a depth electrode 130 that uses the divots 135 as a means to hold the depth electrode 130 at a certain depth relative to the flexible scaffold 102 without the plurality of tines 136 of FIG. 7A. In the illustration of FIG. 7B, the depth electrode 130 defines an outer diameter $diam_1$ of the depth electrode 130 and an inner diameter $diam_2$ that denotes the diameter of the depth electrode 130 at a divot 135. As shown, the thru-hole 126 of the depth electrode port 120 of the flexible scaffold 102 can be appropriately sized to grip the depth electrode 130 at a divot 135 of the plurality of divots 135; for instance, a diameter $diam_3$ of the thru-hole 126 of the depth electrode port 120 can be smaller than the outer diameter $diam_1$ but slightly larger than the inner diameter $diam_2$ of the depth electrode 130 to seat at a selected divot 135 of the plurality of divots 135. Alternatively, in the embodiment of FIG. 7C, the depth electrode 130 can be devoid of divots and defines an outer diameter $diam_4$ of the depth electrode 130. As shown, the thru-hole 126 of the depth electrode port 120 of the flexible scaffold 102 can be appropriately sized to grip the depth electrode 130; for instance, a diameter $diam_5$ of the thru-hole 126 of the depth electrode port 120 can be slightly larger than the outer diameter $diam_4$ of the depth electrode 130 to enable passage of the depth electrode 130 while gripping the depth electrode 130 at a selected position along the depth electrode 130.

As shown in FIGS. 7A-8B, the depth electrodes 130 can be placed at variable depths relative to the flexible scaffold 102. In some embodiments, the plurality of tines 136 can be strategically placed to prevent extraction of the depth electrode 130 and can be used to hold the depth electrode 130 within the tissue at a desired depth relative to the flexible scaffold 102. In particular, the one or more tines 136 of a depth electrode 130 can contact the flexible scaffold 102 from above the depth electrode port 120 (to contact the first surface 104 of the flexible scaffold 102) and/or from below the depth electrode port 120 (to contact the second surface 105 of the flexible scaffold 102). One or more tines 136 of a depth electrode 130 can engage within the target tissue area to enhance stability of the depth electrode 130 within the tissue. Further, in some embodiments, the plurality of tines 136 can be configured to modify a path of the electric field as an insulating material. In one embodiment, a depth electrode 130 can have a collapsing electrode body 131 that would shorten and bow the electrode body 131 to occupy greater surface area to accomplish an enhanced spatial coverage and modify the path of the electric field lines. The one or more divots 135 can also aid in placement of the depth electrode 130 at an intended depth relative to the flexible scaffold 102 by allowing the depth electrode port 120 to grasp the depth electrode 130 at a selected divot 135 of the one or more divots 135.

Figure 8B:
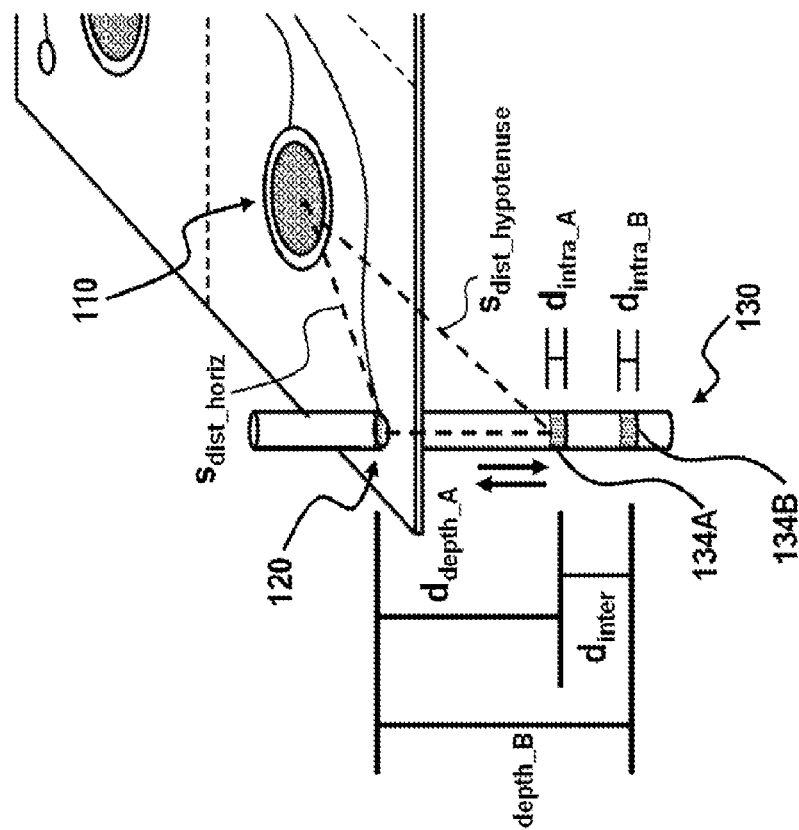
FIGS. 8A and 8B illustrate the depth electrode of FIG. 6 inserted into the flexible scaffold of FIG. 3 at variable depth.
Figure 8A:
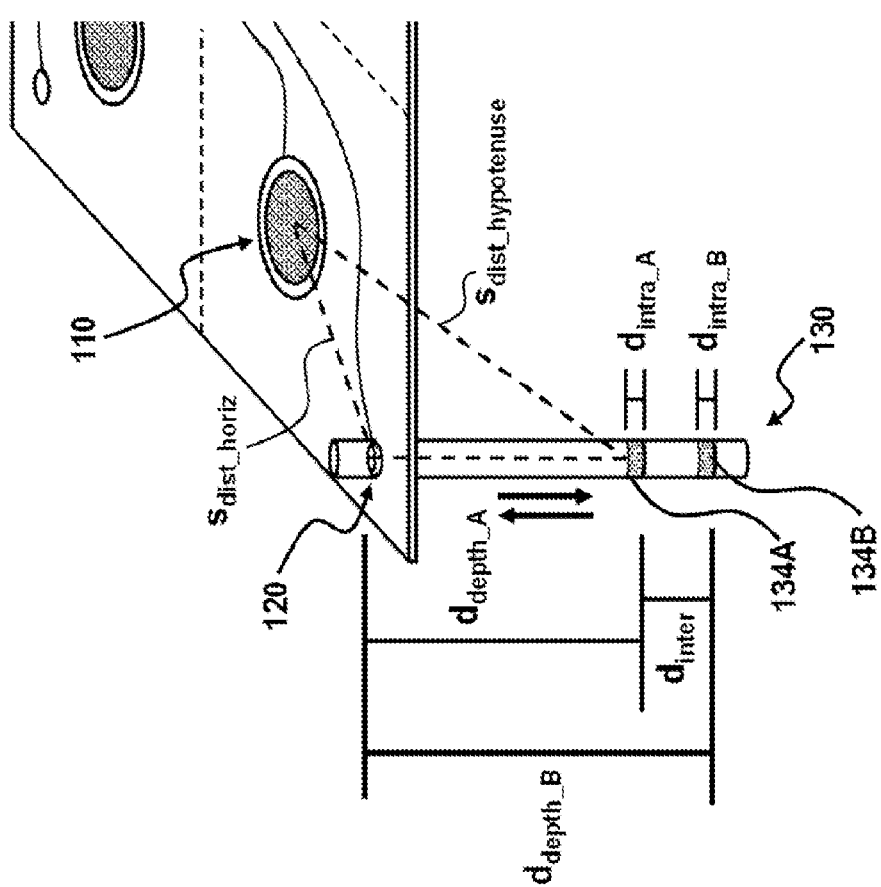

Referring to FIGS. 8A and 8B, the one or more depth electrodes 130 can be placed at variable depth relative to the flexible scaffold 102. Knowledge of inter-contact and intra-contact distances are important to understanding the propagation of the electric field through the target tissue area. FIGS. 8A and 8B illustrate variations of a first depth value $d_{depth\_A}$ that describes a depth of a first terminal contact 134A relative to the flexible scaffold 102, and a second depth value $d_{depth\_B}$ that describes a depth of a second terminal contact 134B relative to the flexible scaffold 102. An inter-contact distance $d_{inter}$ describes a distance between the first terminal contact 134A and the second terminal contact 134B. The first terminal contact 134A defines a first intra-contact distance $d_{intra\_A}$ that describes a distance between a first edge and a second edge of the first terminal contact 134A. Similarly, the second terminal contact 134B defines a second intra-contact distance $d_{intra\_B}$ that describes a distance between a first edge and a second edge of the second terminal contact 134B. It should be noted that while two terminal contacts 134A and 134B are illustrated, the depth electrode 130 can include any number of terminal contacts 134. FIGS. 8A and 8B also define distances between a terminal contact 134 such as terminal contact 134A and an associated surface electrode 110. A horizontal distance $s_{dist\_horiz}$ is defined between the surface electrode 110 and a depth electrode port 120 that holds the depth electrode 130. As discussed above, the depth electrode port 120 can hold the depth electrode 130 such that a terminal contact 134 such as terminal contact 134A defines the first depth value $d_{depth\_A}$ relative to the flexible scaffold 102. As a result, a distance between the surface electrode 110 and terminal contact 134A would be $s_{dist\_hypotenuse}$ defined as a length of a "hypotenuse" of a hypothetical triangle in which lengths of the remaining two sides of the triangle are $s_{dist\_horiz}$ and $d_{depth\_A}$.

Materials contemplated for the depth electrodes 130 include urethane within the elongated electrode body 131 and a conductive material for the interfacing and terminal contacts 132 and 134.

Flexible Scaffold Variations

Figure 9A:
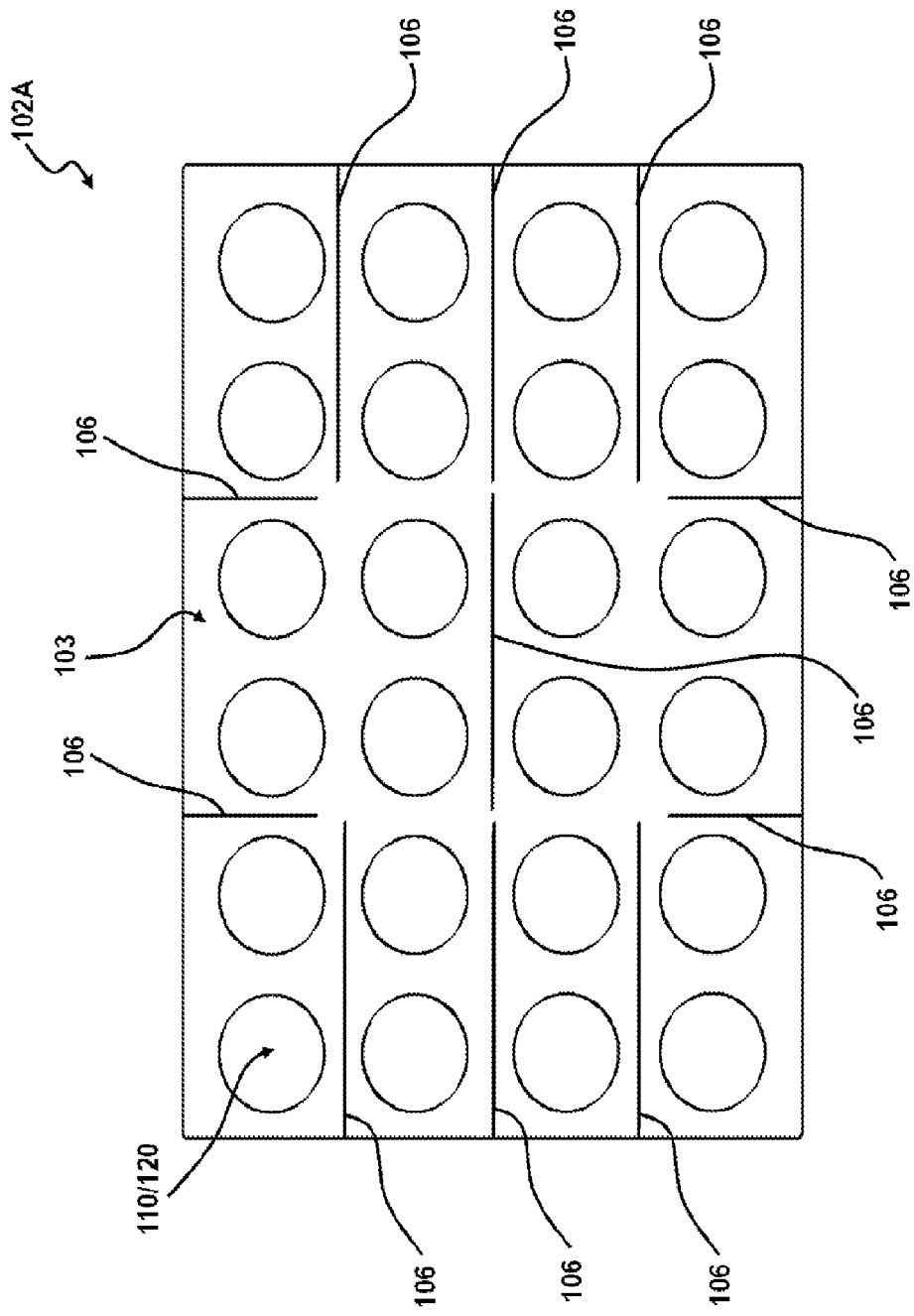
FIGS. 9A-9G are a series of illustrations showing alternative embodiments of the flexible scaffold of FIG. 2.
Figures 9B, 9C:
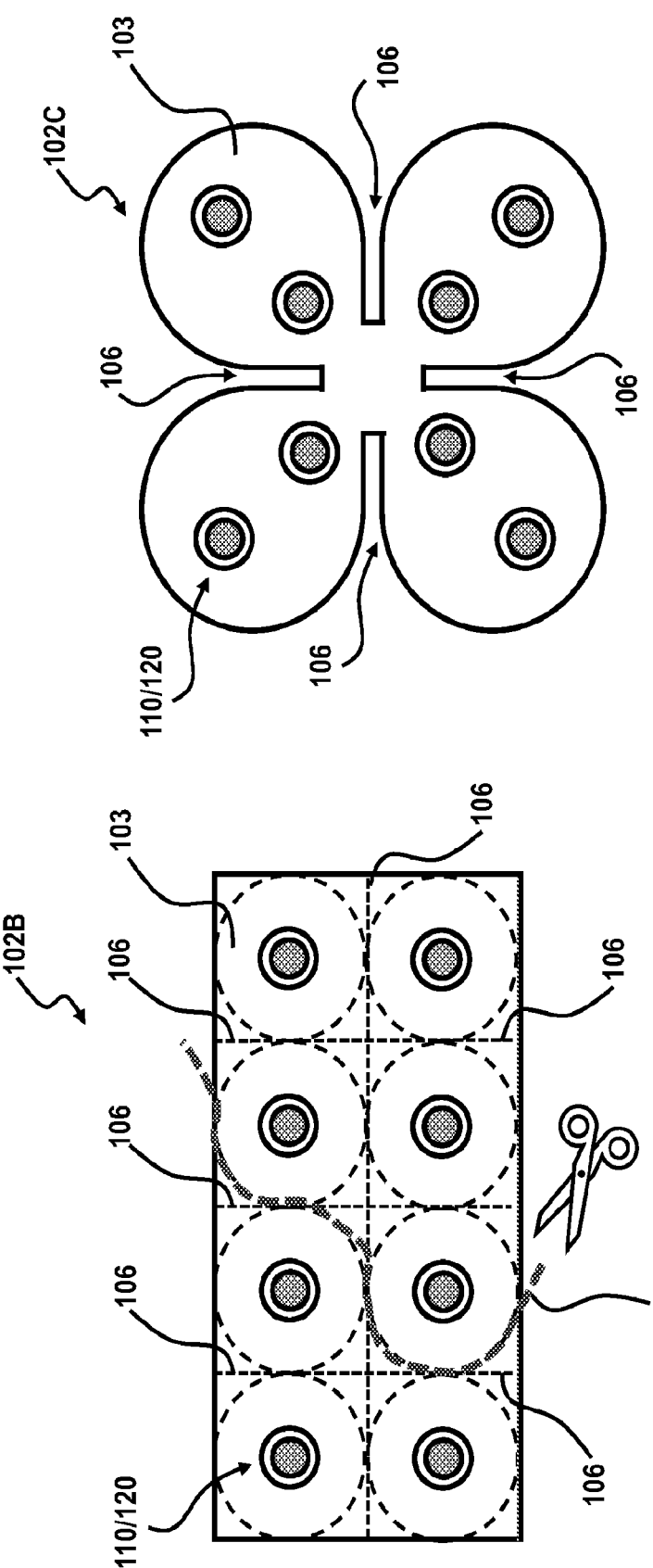
Figure 9E:
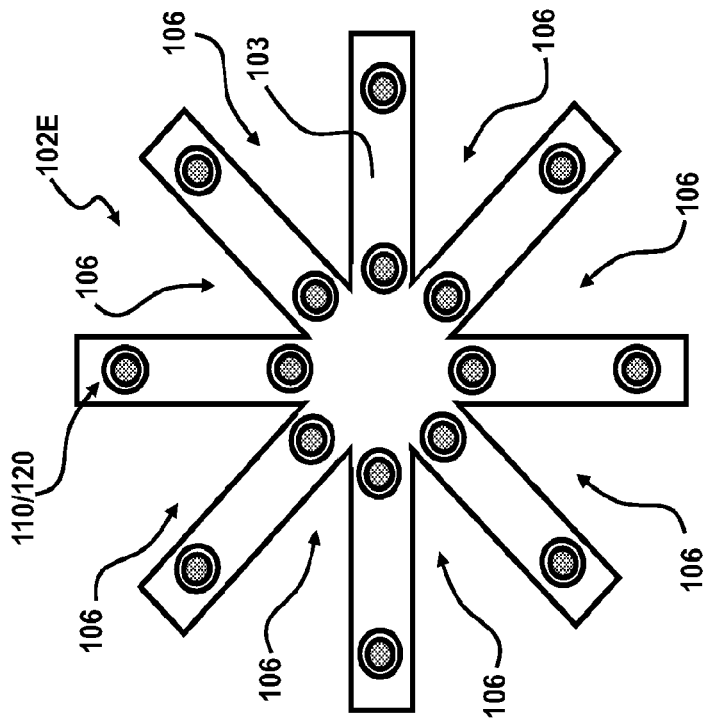
Figure 9D:
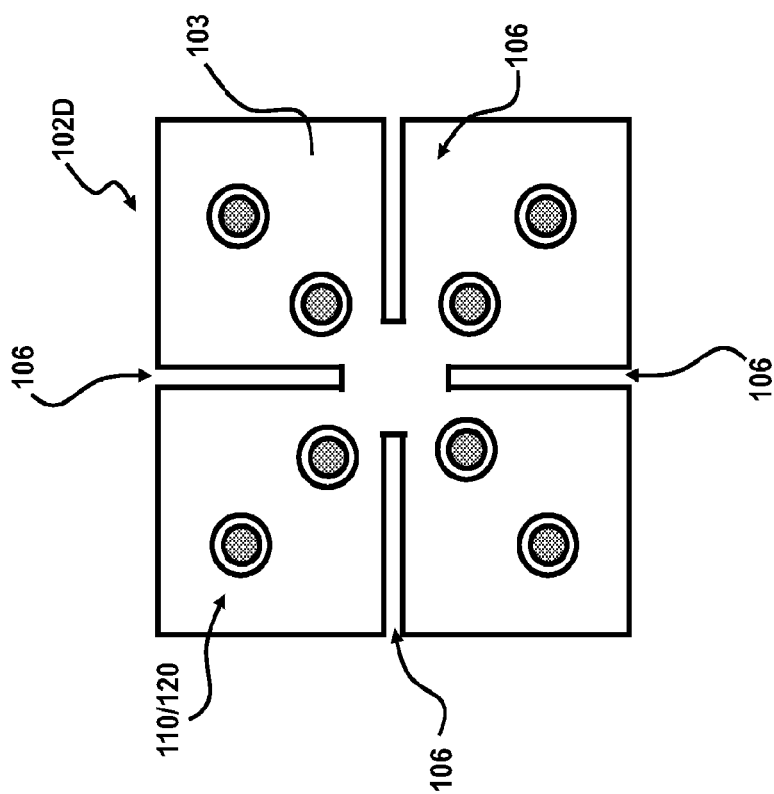
Figure 9G:
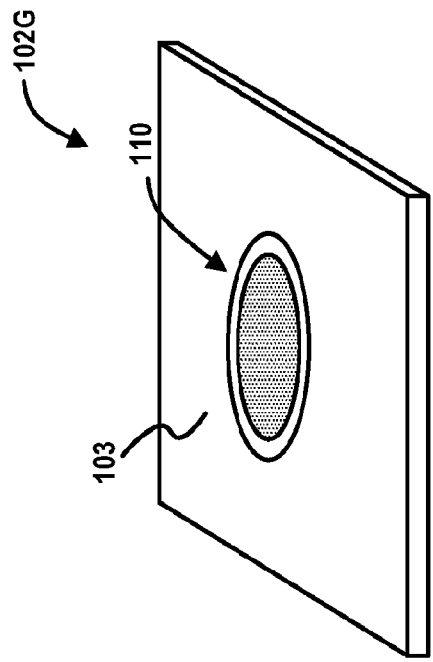
Figure 9F:
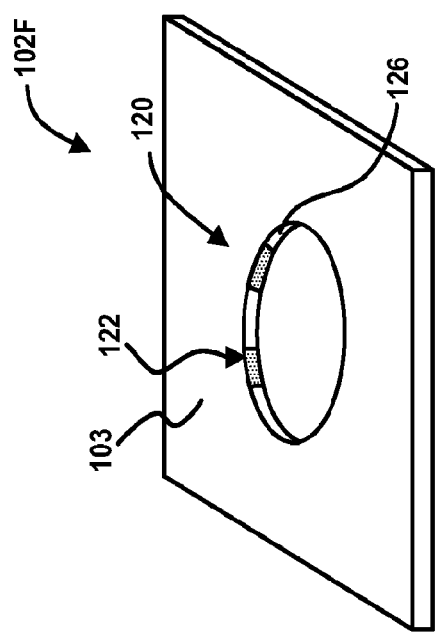

FIGS. 9A-9G illustrate variations of the flexible scaffold 102. FIG. 9A in particular illustrates a flexible scaffold 102A that provides an elongated planar body 103 featuring a plurality of surface electrodes 110 or depth electrode ports 120 and a plurality of perforations 106. FIG. 9B illustrates a flexible scaffold 102B that similarly provides an elongated planar body 103 in an alternate configuration with a plurality of surface electrodes 110 or depth electrode ports 120. As shown, the flexible scaffold 102B of FIG. 9B provides both straight and rounded perforations 106 and illustrates the option of cutting the flexible scaffold 102B to size/shape along line A. FIG. 9C illustrates a variation of the flexible scaffold 102C featuring a rounded planar body 103 with a plurality of surface electrodes 110 or depth electrode ports 120 in an alternate arrangement. As shown, a plurality of perforations 106 of FIG. 9C are characterized as gaps that separate sections of the flexible scaffold 102C. FIG. 9D shows a similar variation of the flexible scaffold 102D that provides a squared-off planar body 103 with a plurality of surface electrodes 110 or depth electrode ports 120 and a plurality of perforations 106 are characterized as gaps that separate sections of the flexible scaffold 102D, similar to that of FIG. 9C. FIG. 9E illustrates a further variation where the flexible scaffold 102E defines a star-shaped planar body 103 with a plurality of surface electrodes 110 or depth electrode ports 120 disposed thereon. The plurality of perforations 106 of the flexible scaffold 102E are characterized as large gaps between sections of the planar body 103. FIG. 9F illustrates a variation where the flexible scaffold 102F defines planar body 103 with a single depth electrode port 120 disposed thereon, with thru-hole 126 and port contacts 122 visible. FIG. 9G illustrates a further variation where the flexible scaffold 102G defines a planar body 103 with a single surface electrode 110 disposed thereon.

FIGS. 10A and 10B show variations of the flexible scaffold 102, particularly alternative depth electrode ports 120. Flexible scaffold 102F includes a depth electrode port 120 featuring a gradual directing tube 124 along the second surface 105 in the form of a thru-hole built into the flexible scaffold 102. For instance, the flexible scaffold 102 can thicken in regions where the directing tube 124 is present to avoid overhang of the directing tube 124 outside the flexible scaffold 102. In the flexible scaffold 102G of FIG. 10B, the directing tube 124 is angled to hold a depth electrode 130 at an angle (between 0 and 90 degrees) below the surface of the flexible scaffold 102. As shown, the corresponding port contacts 122 are also defined at the same angle as the directing tube 124 to ensure proper contact between the port contacts 122 and a depth electrode.

Control System

The flexible scaffold 102 and the associated surface electrodes 110 and depth electrodes 130 communicate with a control system 200 that provides and modulates power ($V_{out}$) to each associated surface electrode 110 and depth electrode 130. Additionally, the control system 200 can also measure the resultant electric field within the tumor bed through voltage measurement ($V_{in}$) through one or more surface electrodes 110 and/or depth electrodes 130. In some embodiments, the control system 200 is operable to adjust various waveform parameters applied to connected surface electrodes 110 and depth electrodes 130 based on measured feedback received from the surface electrodes 110 and/or depth electrodes 130 to optimize the applied electric field.

In some embodiments, the control system 200 is operable to recognize each of the connected surface electrodes 110 or depth electrodes 130 and can configure the resultant electric field based on the connected surface electrodes 110 or depth electrodes 130. For instance, the control system 200 can recognize one or more "groups" of surface electrodes 110 which can be represented at a waveform generator 230 of the control system 200 to adopt a modular schematic for configuring (and pairing for phase shifting of a waveform) various surface electrodes 110 and depth electrodes 130 within a selected grouping. This may be achieved using multiplexors or another strategy for managing arrays of electrodes 110 and 130. In a primary embodiment, the control system 200 is operable to recognize when one or more surface electrodes 110 are not connected, either because they have been deliberately disconnected by the practitioner or because they are not making appropriate contact with the target tissue area. For instance, control system 200 can detect shorts that correspond with wiring that was cut, and correspondingly avoid stimulation or measurement within those electrode wires.

Pinout and Electrical Connection Example

Figure 11:
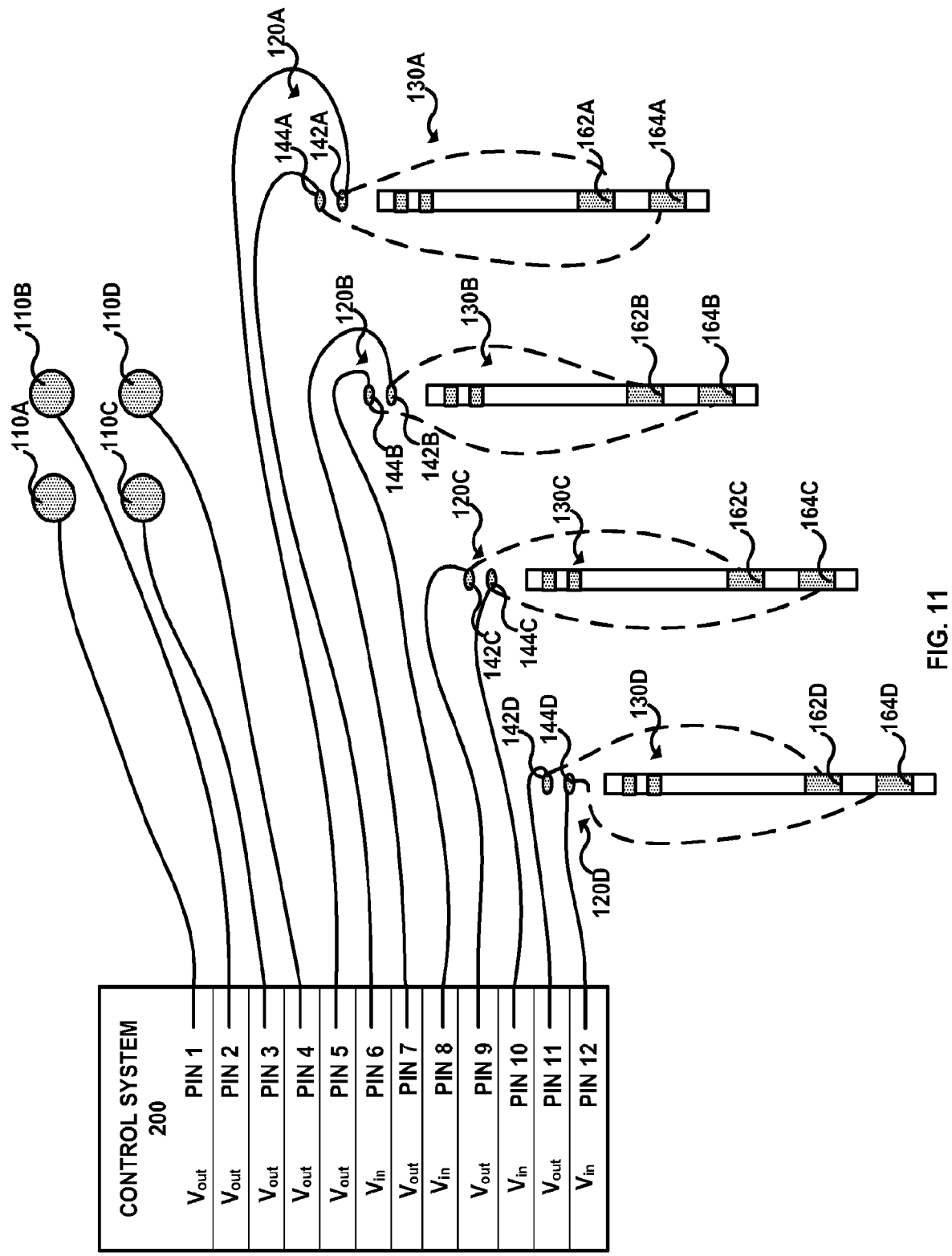
FIG. 11 is a simplified diagram showing electrical connections between the control system and the plurality of electrodes of FIG. 1.

In one non-limiting example, FIG. 11 illustrates connections between four surface electrodes 110A-D and four depth electrode ports 120A-D (flexible scaffold 102 not illustrated). In this example, consider the surface electrodes 110A-D being configured for applying a voltage to the target tissue area through direct contact with a surface of the target tissue area. Further, consider the depth electrode ports 120A-D being configured, when electrically coupled with corresponding depth electrodes 130A-D, for applying a voltage to the target tissue area and also for measuring a voltage applied to the target tissue area. Depth electrodes 130A-D can each include a plurality of terminal contacts 134, which include a respective stimulating contact 162 and a measuring contact 164; stimulating and measuring contacts 162 and 164 can be located at different positions along the length of the associated depth electrode 130. Depth electrode ports 120A-120D of the flexible scaffold 102 can include stimulating port contacts 142 and measuring port contacts 144 of a port contact 122 for communicating stimulating voltages and measured voltages between the depth electrodes 130A-D and the control system 200.

An example pinout scheme of control system 200 is provided:

- Pin 1 of control system 200 is "V_out" for a first surface electrode 110A;
- Pin 2 of control system 200 is "V_out" for a second surface electrode 110B;
- Pin 3 of control system 200 is "V_out" for a third surface electrode 110C;
- Pin 4 of control system 200 is "V_out" for a fourth surface electrode 110D;
- Pin 5 of control system 200 is "V_out" for a first depth electrode port 120A which corresponds to a stimulating port contact 142A of the port contact 122 of the first depth electrode port 120A, which couples with a stimulating contact 162A of the first depth electrode 130A electrically coupled to the first depth electrode port 120A;
- Pin 6 of control system 200 is "V_in" for a first depth electrode port 120A which corresponds to a measuring port contact 144A of the port contact 122 of the first depth electrode port 120A, which couples with a measuring contact 164A of the first depth electrode 130A electrically coupled to the first depth electrode port 120A;
- Pin 7 of control system 200 is "V_out" for a second depth electrode port 120B which corresponds to a stimulating port contact 142B of the port contact 122 of the second depth electrode port 120B, which couples with a stimulating contact 162B of the second depth electrode 130B electrically coupled to the second depth electrode port 120B;
- Pin 8 of control system 200 is "V_in" for a second depth electrode port 120B which corresponds to a measuring port contact 144B of the port contact 122 of the second depth electrode port 120B, which couples with a measuring contact 164B of the second depth electrode 130B electrically coupled to the second depth electrode port 120B;
- Pin 9 of control system 200 is "V_out" for a third depth electrode port 120C which corresponds to a stimulating port contact 142C of the port contact 122 of the third depth electrode port 120C, which couples with a stimulating contact 162C of the third depth electrode 130C electrically coupled to the third depth electrode port 120C;
- Pin 10 of control system 200 is "V_in" for a third depth electrode port 120C which corresponds to a measuring port contact 144C of the port contact 122 of the third depth electrode port 120C, which couples with a measuring contact 164C of the third depth electrode 130C electrically coupled to the third depth electrode port 120C;
- Pin 11 of control system 200 is "V_out" for a fourth depth electrode port 120D which corresponds to a stimulating port contact 142D of the port contact 122 of the fourth depth electrode port 120D, which couples with a stimulating contact 162D of the fourth depth electrode 130D electrically coupled to the fourth depth electrode port 120D;
- Pin 12 of control system 200 is "V_in" for a fourth depth electrode port 120D which corresponds to a measuring port contact 144D of the port contact 122 of the fourth depth electrode port 120D, which couples with a measuring contact 164D of the fourth depth electrode 130D electrically coupled to the fourth depth electrode port 120D;

Pins designated "V_out" indicate that a stimulating voltage is applied to the target tissue area through the associated electrode 110 or 130 by the control system 200.

Pins designated "V_in" indicate that a measured voltage is received from the target tissue area through the associated electrode 110 or 130 by the control system 200.

Control system 200 can provide additional "V_in" pins or, optionally, can change the roles of pins associated with surface electrodes 110A-110D to enable receipt of a measured voltage value, if one or more surface electrodes 110 are to be used for measuring the electric field. This could also be useful for enabling the control system 200 to recognize when one or more surface electrodes 110 are not connected, either because they have been deliberately disconnected by the practitioner or because they are not making appropriate contact with the surface of the target tissue area.

Control system 200 can measure aspects of the resultant electric field propagating through the target tissue area through "V_in" pins that are electrically coupled with an electrode 110 or 130 configured in a "measuring" role for providing feedback to the control system 200. Based on measured values, the control system 200 can optimize the alternating electric field applied to the target tissue area through "V_out" pins that are electrically coupled with surface electrodes 110 or depth electrodes 130 configured in a "stimulating" role. This may involve changing or updating "V_out" values or other parameters for individual electrodes 110 or 130 or whole groups of electrodes 110 or 130

Generalized Electrical Connections

Figure 12:
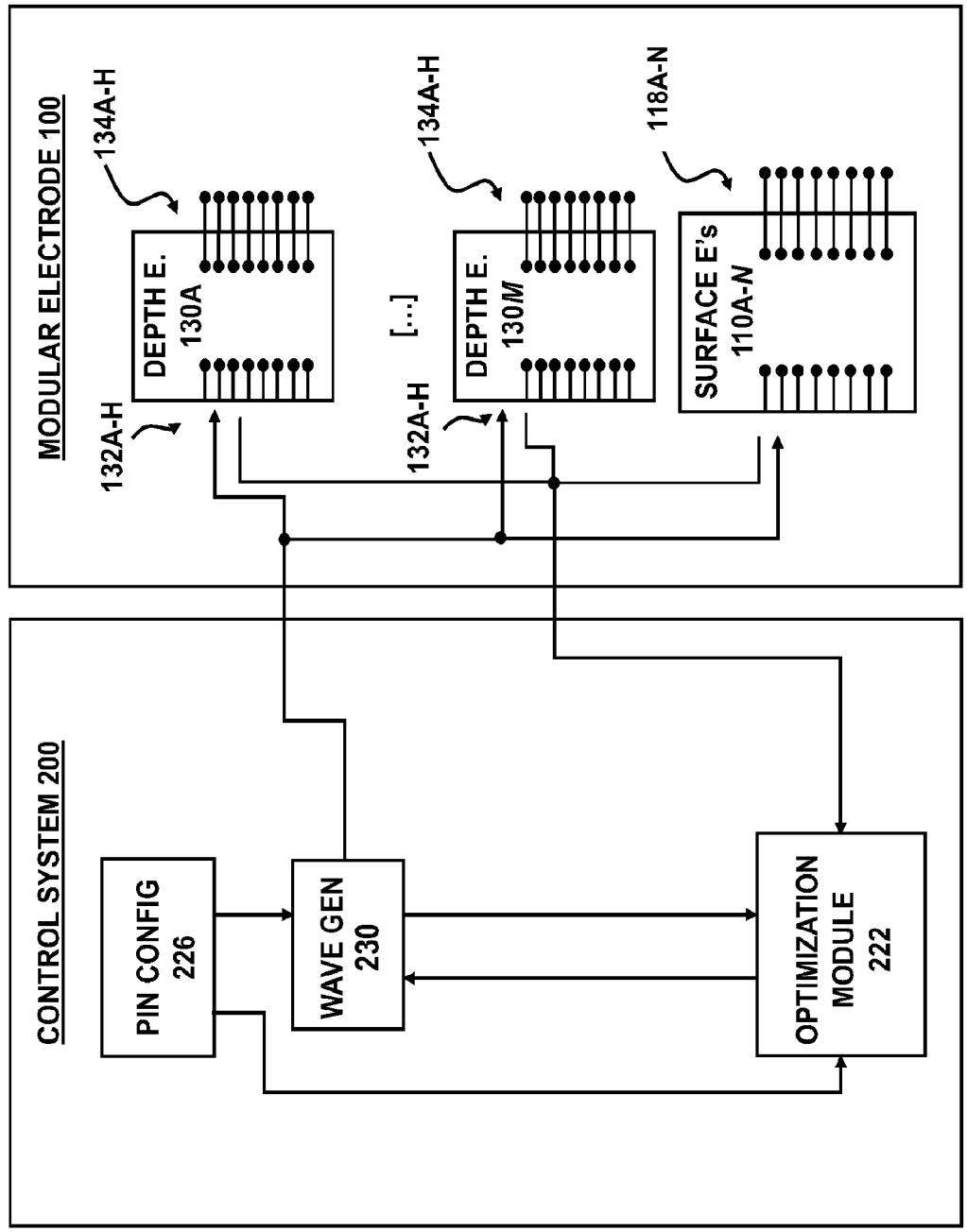
FIG. 12 is a simplified diagram showing data flow between the control system and the modular electrode of FIG. 1.

FIGS. 1 and 12 show connections between the control system 200 and the modular electrode 100. In the example, modular electrode 100 has been generalized to feature an array of M depth electrodes 130 each having an array of H contacts 134, and to additionally feature an array of N surface electrodes 110 each defining a respective surface contact 118 for a total of N surface contacts 118A-N, where the values of M, H and N can be selected by the practitioner. As shown, the control system 200 includes a pin configuration module 226 as part of an Alternating Electric Field Processes/services application 290 stored within the control system 200 that assigns stimulating or measuring roles to each respective pin and consequently, each respective electrode 110 or 130. Pin configuration module 226 can optionally provide information related to a current layout or arrangement of the electrodes 110 and 130.

As shown, pin configuration module 226 communicates with a waveform generator 230 that generates a respective applied stimulus for one or more "stimulating" contacts 118 or 132 of the associated electrode 110 or 130 based on the role assignments provided by the pin configuration module 226. The generated waveforms are passed to the modular electrode 100 and to their assigned depth electrode 130 or surface electrode 110. In the case of a depth electrode 130 of the one or more depth electrodes 130A-M that include one or more terminal contacts 134A-H assigned to a "stimulating" role, the generated waveforms are passed to one or more of the interfacing contacts 132A-H of the respective depth electrode 130A-M through the depth electrode ports 120 (illustrated in FIG. 11) which in turn pass the generated waveform to one or more associated terminal contacts 134A-H for delivery to the target tissue area. In the case of a surface electrode 110 of the one or more surface electrodes 110A-N that each respectively include an associated surface contact 118 of the one or more surface contacts 118A-N assigned to a "stimulating" role, the generated waveforms are passed to one or more of the surface contacts 118A-N for delivery to the target tissue area. Briefly referencing back to FIGS. 4B and 6, the one or more port contacts 122 can assume the role of a measuring port contact 144 or a stimulating port contact 142, the one or more interfacing contacts 132A-H can assume the role of a measuring interfacing contact 154 or a stimulating interfacing contact 152, and the one or more terminal contacts 134A-H can assume the role of a measuring terminal contact 164 or a stimulating terminal contact 162.

Pin configuration module 226 also communicates with an optimization module 222 that receives a respective measured voltage value from one or more "measuring" contacts 118 or 134 of the associated electrode 110 or 130 based on the role assignments provided by the pin configuration module 226. The received voltages are passed to the modular electrode 100 from one or more depth electrodes 130 or surface electrodes 110. In the case of a depth electrode 130 of the one or more depth electrodes 130A-M that include one or more terminal contacts 134A-H assigned to a "measuring" role, the received voltages are passed to one or more of the interfacing contacts 132A-H of the respective depth electrode 130A-M from one or more associated terminal contacts 134A-H in contact with the target tissue area. Interfacing contacts 132A-H assigned to "measuring" roles relay the measured voltages through the depth electrode ports 120 (illustrated in FIG. 11) which in turn pass the received voltage to back to the control system 200, which includes an optimization module 222 that optimizes the applied stimulating voltages based on feedback received in the form of resultant voltage values from within the target tissue area. In the case of a surface electrode 110 of the one or more surface electrodes 110A-N that each respectively include an associated surface contact 118 of the one or more surface contacts 118A-N assigned to a "measuring" role, the measured voltages from the target tissue area are passed to the control system 200 which includes the optimization module 222.

In some embodiments, the optimization module 222 compares the measured voltages received from the one or more electrodes 110 or 130 assigned to "measuring" roles with one or more target voltage values that represent proper electric field strength and direction values for therapeutic treatment of the target tissue area. Based on this comparison, optimization module 222 can adjust one or more waveform parameters of the waveform generator 230 to modulate the stimulating voltage applied by the one or more electrodes 110 or 130 applied to "stimulating" roles.

In a further embodiment, the control system 200 can identify one or more unconnected pins or contacts 118, 132, 134 of the one or more electrodes 110 or 130 through short detection or another method. Such a situation may arise when one or more contacts 118 or 134 have been deliberately removed or disconnected by the practitioner, or if the one or more contacts 118 or 134 are not making proper contact with the target tissue area. User Interface module 224 (FIG. 1) can display one or more alerts denoting the unconnected pins or contacts 118, 132, 134 to inform the practitioner. The practitioner can then "approve" one or more intentionally unconnected pins or contacts 118, 132, 134, and the control system 200 will subsequently turn off the one or more intentionally unconnected pins or contacts 118, 132, 134. If the one or more unconnected pins or contacts 118, 132, 134 are not intentionally disconnected, then the practitioner can adjust a position of the associated electrode 110 or 130 until proper contact is made or can alternatively switch the associated electrode 110 or 130 out for a new one.

Process

Referring to FIGS. 13A-13D, a process flow 300 is illustrated that outlines a method for applying and optimizing a therapeutic electric field applied to a target tissue area using the modular electrode 100 and the control system 200. At block 310 of process flow 300 shown in FIGS. 13A and 13B, a practitioner selects or cuts the modular electrode 100 to a desired shape or size based on physiological need of the target tissue area. At sub-block 311 of block 310, the practitioner optionally cuts the flexible scaffold 102 to shape/size. At sub-block 312 of block 310, the practitioner optionally cuts one or more depth electrodes 130 to shape/size. At sub-block 313 of block 310, the practitioner optionally adjusts one or more tines 136 to an appropriate shape and/or position along the one or more depth electrodes 130. At sub-block 314 of block 310, the practitioner inserts the one or more depth electrodes 130 into a respective depth electrode port 120 of the flexible scaffold 102 to a necessary depth. At block 320 of process flow 300, the practitioner couples the modular electrode 100 with the target tissue area.

Figure 13A:
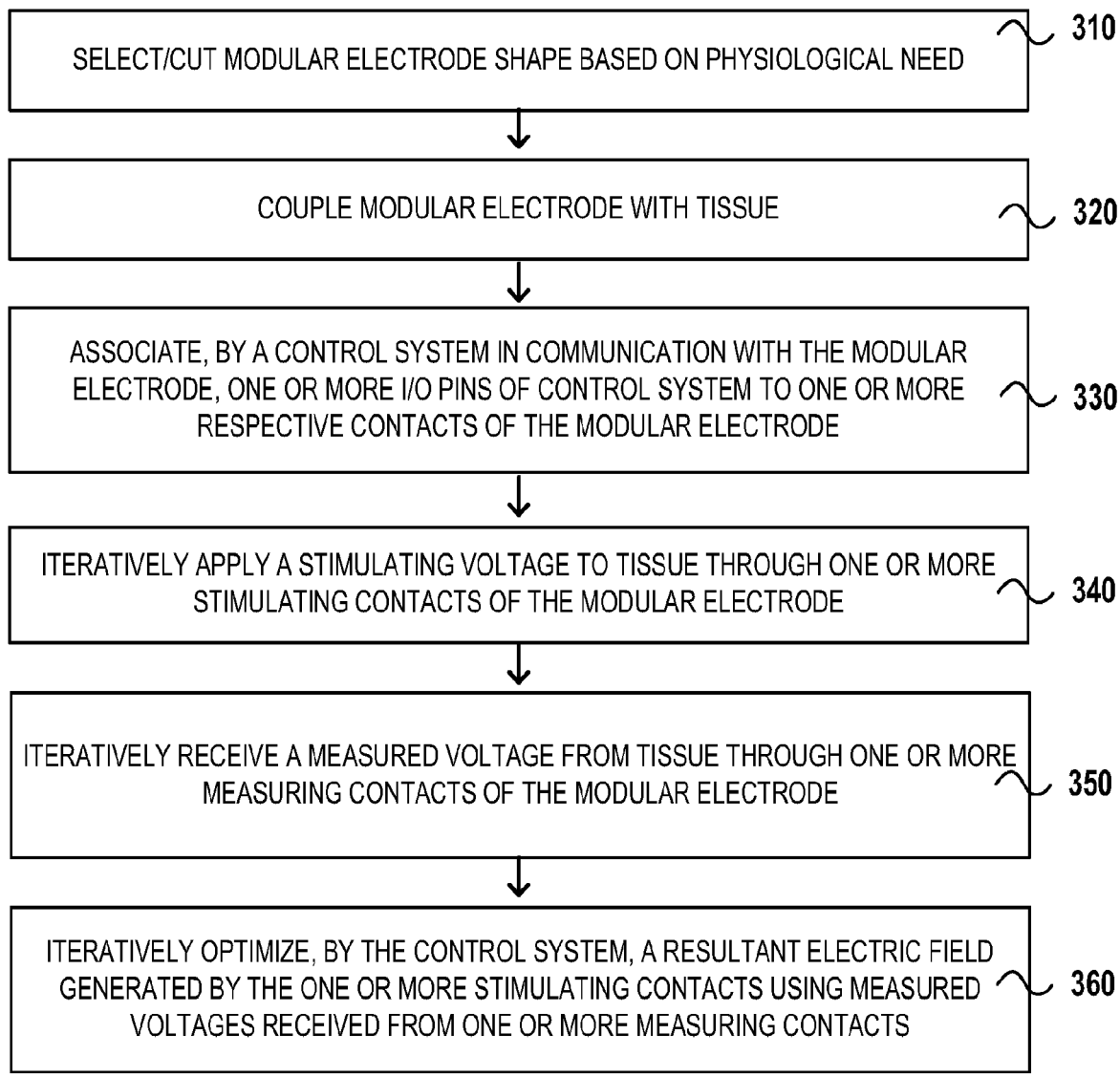
FIGS. 13A-13D are a series of process flows showing a process for application of a therapeutic electric field to a targeted tissue area.
Figure 13B:
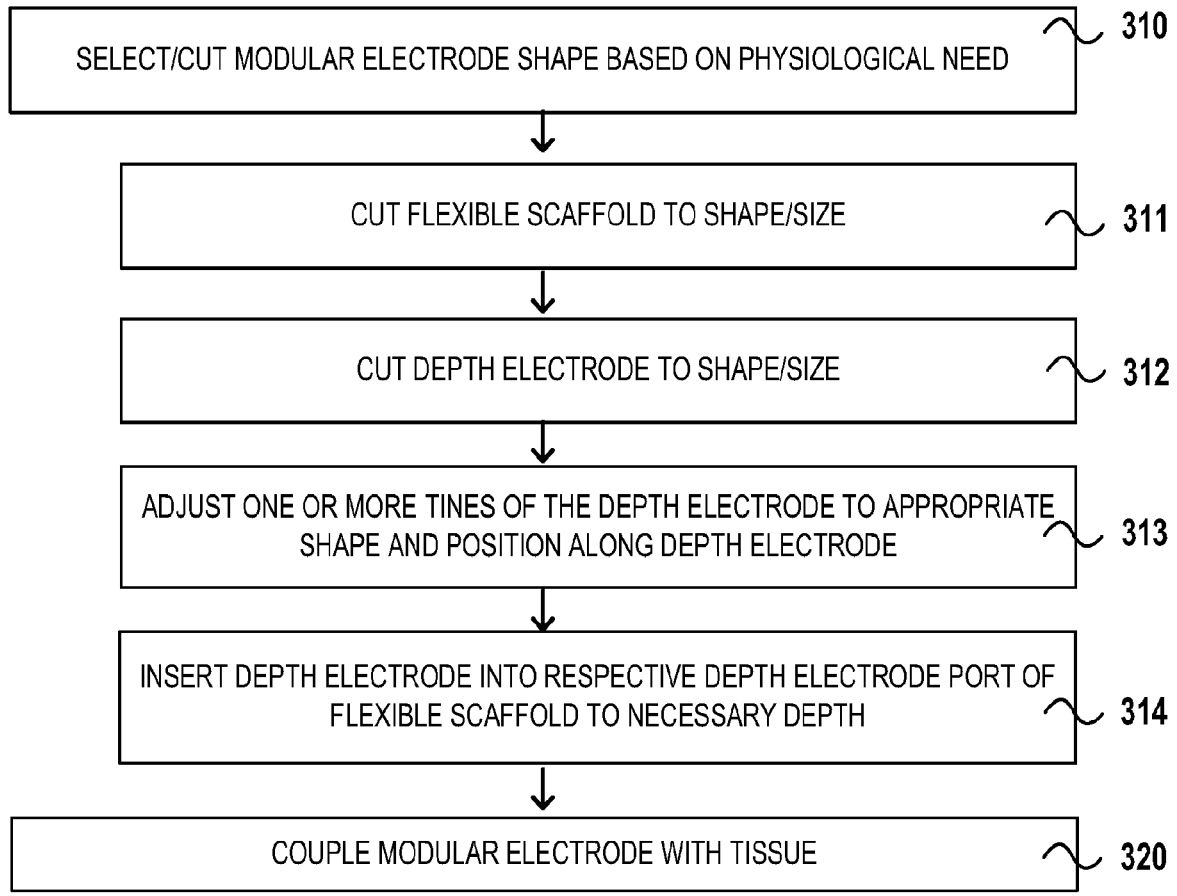
Figure 13C:
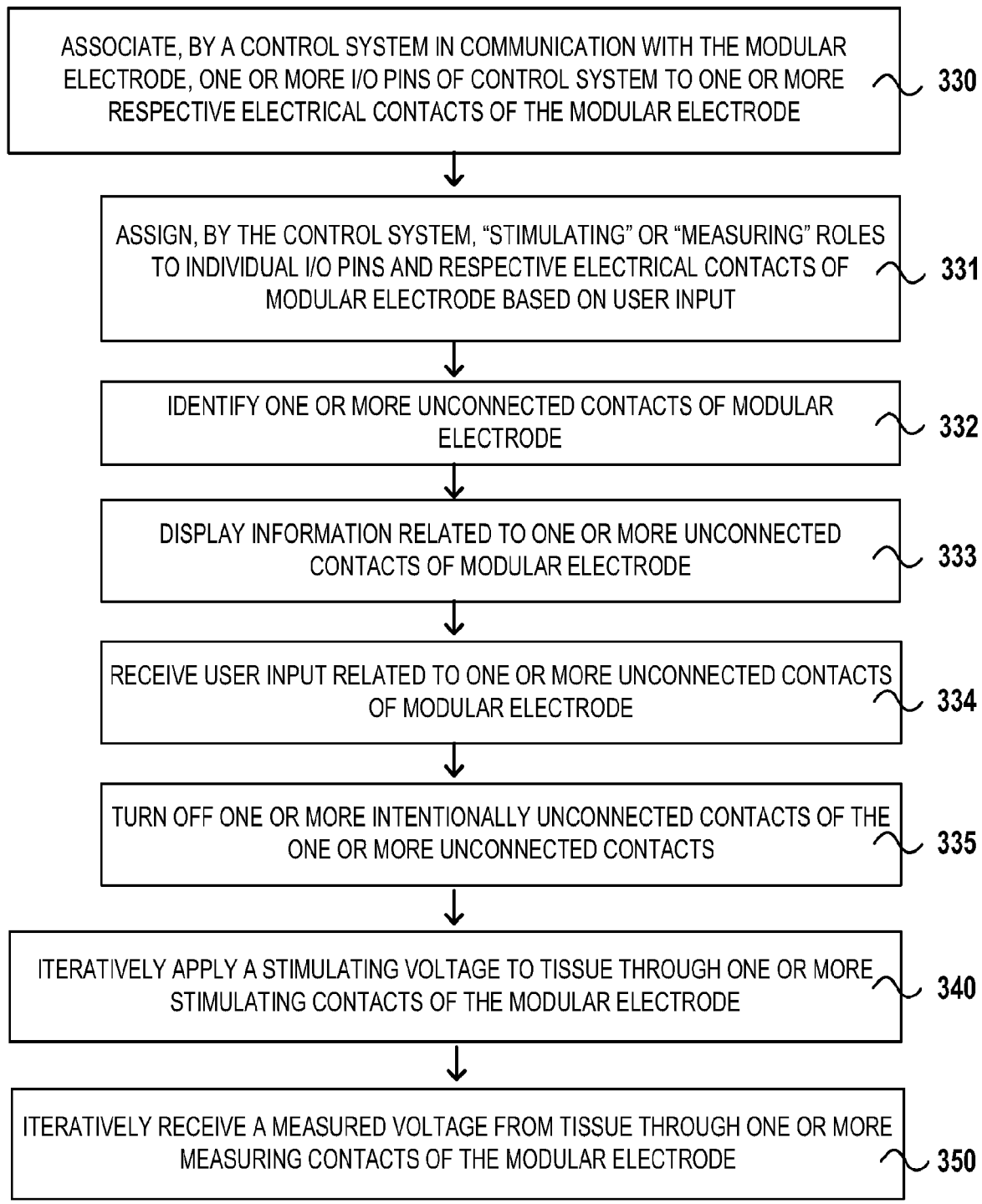
Figure 13D:
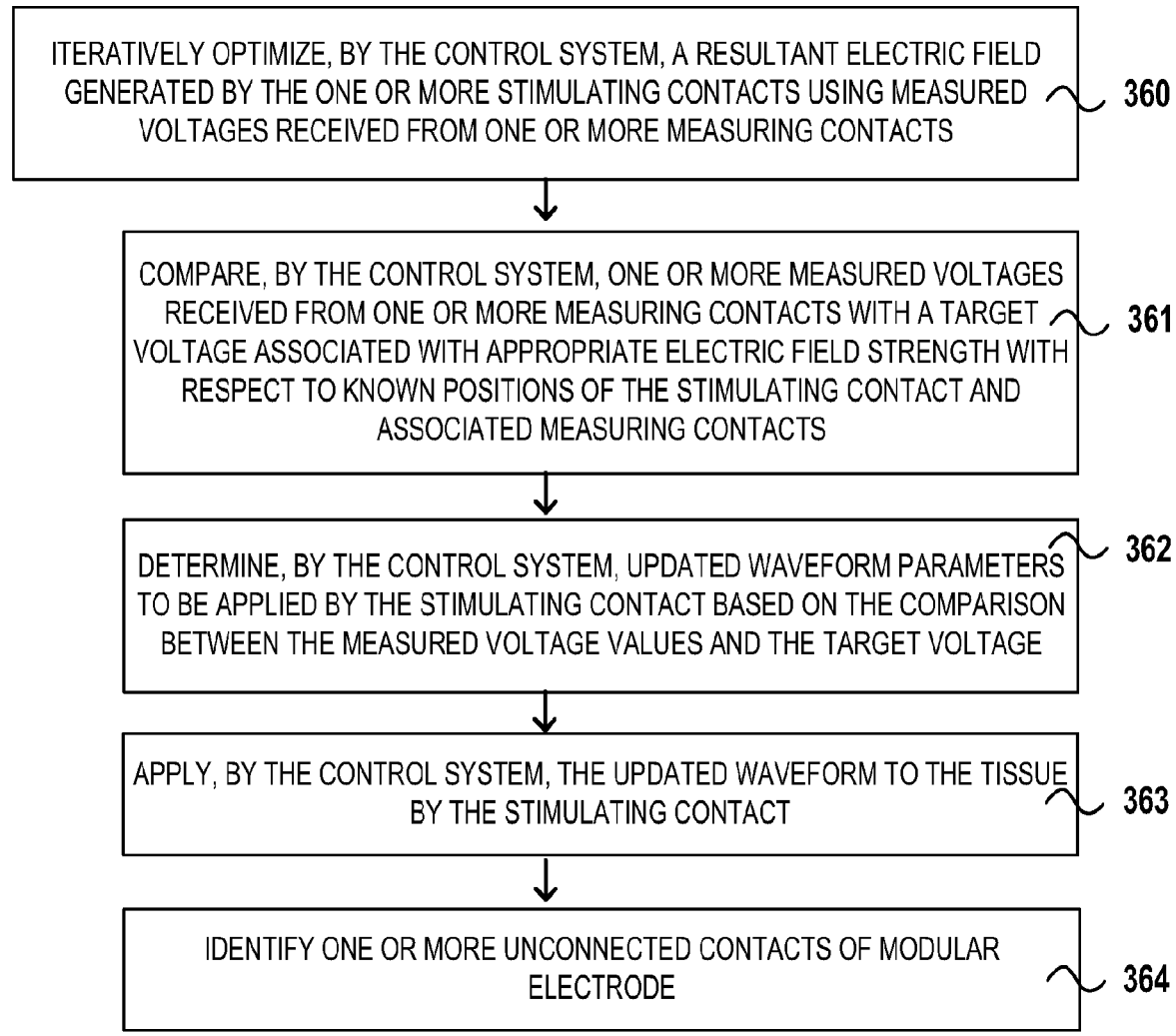

At block 330 of process flow 300 illustrated in FIGS. 13A and 13C, the control system 200 in communication with the modular electrode 100 associates one or more pins of the control system 200 to one or more respective contacts 118, 132, 134 of the modular electrode 100. At sub-block 331 of block 330, the control system 200 assigns "stimulating" or "measuring" roles to individual pins and respective contacts 118, 132, 134 of the modular electrode 100 based on user input. At sub-block 332 of block 330, the control system 200 identifies one or more unconnected contacts 118, 132, 134 of the modular electrode 100. At sub-block 333 of block 330, the control system 200 displays information related to the one or more unconnected contacts 118, 132, 134 of the modular electrode 100. At sub-block 334 of block 330, the control system 200 receives user input related to the one or more unconnected contacts 118, 132, 134 of the modular electrode 100, which can include indications that one or more of the unconnected contacts 118, 132, 134 are intentionally disconnected by the practitioner. At sub-block 335 of block 330, the control system 200 then turns off one or more intentionally unconnected contacts 118, 132, 134 of the modular electrode 100.

At block 340 of process flow 300 illustrated in FIGS. 13A and 13C, the control system 200 iteratively applies a stimulating voltage to the target tissue area through the one or more surface electrodes 110 and/or one or more depth electrodes 130 of the modular electrode 100. At block 350 of process flow 300 illustrated in FIG. 13A, the control system 200 iteratively receives a measured voltage value from the target tissue area through the one or more surface electrodes 110 and/or one or more depth electrodes 130 of the modular electrode 100. At block 360 of process flow 300 illustrated in FIGS. 13A and 13D, the control system 200 iteratively optimizes a resultant electric field generated by the one or more electrodes 110 and/or 130 assigned to "stimulating" roles using measured voltages received from the one or more electrodes 110 and/or 130 assigned to "measuring" roles. At sub-block 361 of process flow 300 illustrated in FIG. 13D, the control system 200 compares one or more measured voltages received from one or more electrodes 110 and/or 130 assigned to "measuring" roles with a target voltage value associated with appropriate electric field strength with respect to known positions of each respective contact 118, 132, 134 of the one or more electrodes 110 and/or 130. At sub-block 362 of process flow 300, the control system 200 determines one or more updated waveform parameters to be applied by the one or more electrodes 110 and/or 130 assigned to "stimulating" roles based on the comparison between the measured voltage values and the target voltage values. At sub-block 363 of process flow 300, the control system 200 applies an updated stimulating voltage based on the one or more updated waveform parameters to the target tissue area through the one or more electrodes 110 and/or 130 assigned to "stimulating" roles. Optionally, throughout this process, at sub-block 364 of process flow 300, the control system 200 repeatedly checks if one or more unconnected contacts 118, 132, 134 in case connection is lost.

Method of Manufacture

Figure 14:
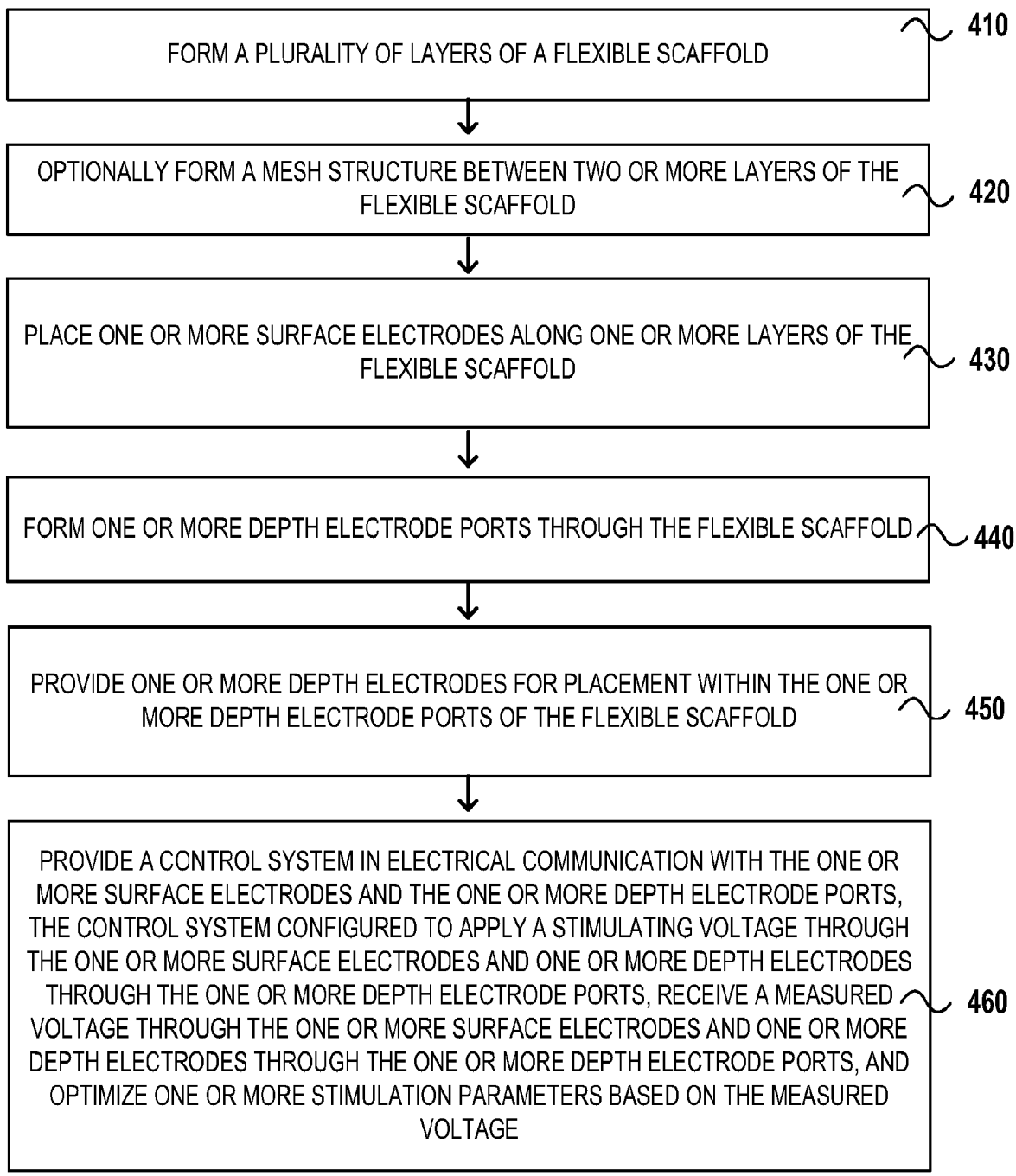
FIG. 14 is a process flow showing a method of manufacture of the modular electrode of FIG. 1.

Referring to FIG. 14, a process flow 400 is illustrated that provides a method of manufacture of the modular electrode 100. At block 410 of process 400, the process includes forming a plurality of layers 108 of a flexible scaffold 102. At block 420, process 400 optionally includes forming a mesh structure 109 between two or more layers 108 of the flexible scaffold 102. At block 430, process 400 includes placing one or more surface electrodes 110 along one or more layers 108 of the flexible scaffold 102. At block 440, process 400 includes forming one or more depth electrode ports 120 through the flexible scaffold 102. At block 450, process 400 includes providing one or more depth electrodes 130 for placement within the one or more depth electrode ports 120 of the flexible scaffold 102. At block 460, process 400 includes provide a control system 200 in electrical communication with the one or more surface electrodes 110 and the one or more depth electrode ports 120, the control system 200 configured to: apply a stimulating voltage through the one or more surface electrodes 110 and one or more depth electrodes 130 through the one or more depth electrode ports 120, receive a measured voltage through the one or more surface electrodes 110 and one or more depth electrodes 130 through the one or more depth electrode ports 120, and optimize one or more stimulation parameters based on the measured voltage.

Computer-Implemented System

Figure 15:
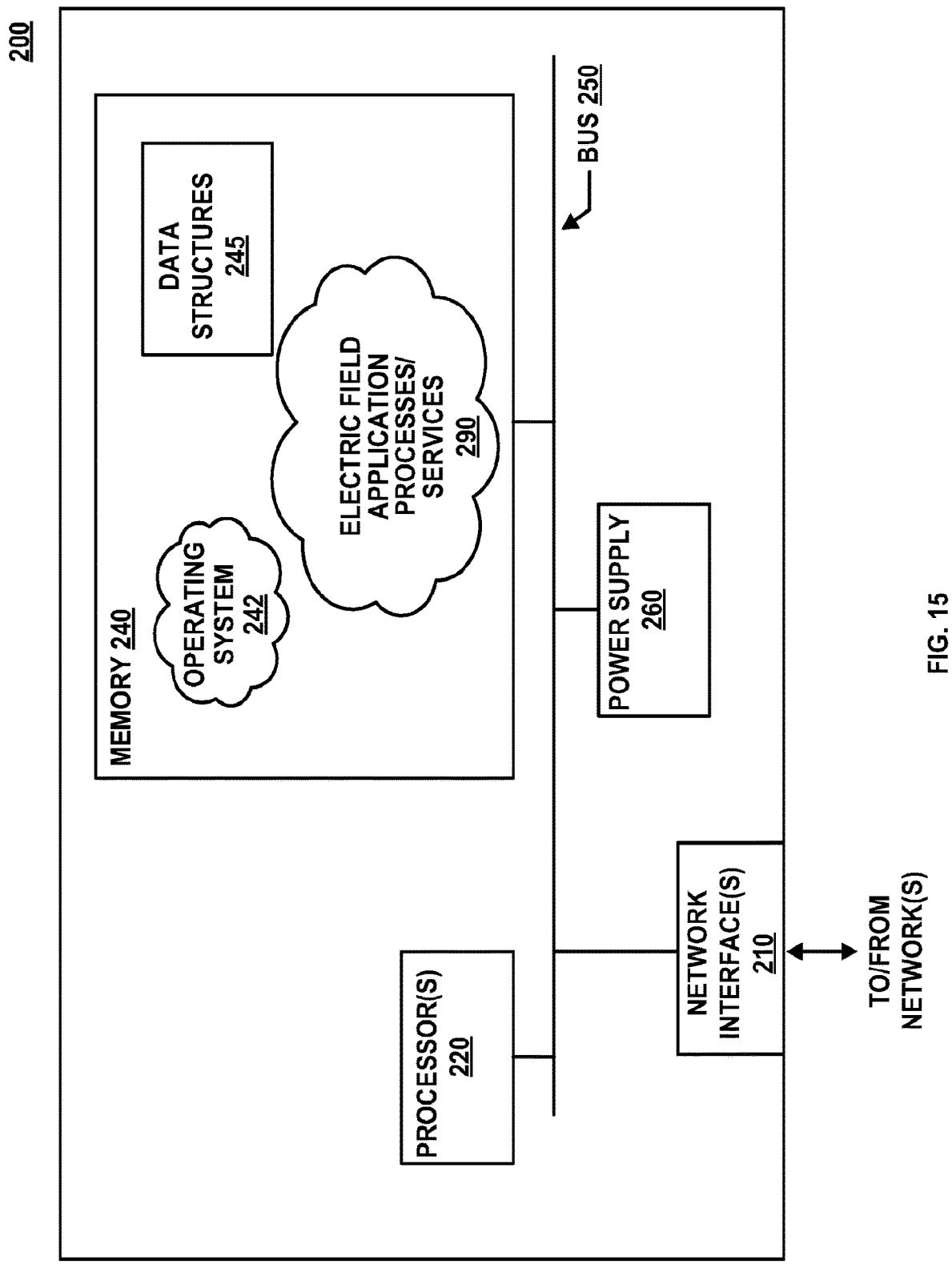
FIG. 15 is a simplified diagram showing an exemplary computing system for implementation of the system of FIG. 1.

FIG. 15 is a schematic block diagram of an example system 200 that may be used with one or more embodiments described herein, e.g., as control system 200 shown in FIG. 1.

System 200 comprises one or more network interfaces 210 (e.g., wired, wireless, PLC, etc.), at least one processor 220, and a memory 240 interconnected by a system bus 250, as well as a power supply 260 (e.g., battery, plug-in, etc.).

Network interface(s) 210 include the mechanical, electrical, and signaling circuitry for communicating data over the communication links coupled to a communication network. Network interfaces 210 are configured to transmit and/or receive data using a variety of different communication protocols. As illustrated, the box representing network interfaces 210 is shown for simplicity, and it is appreciated that such interfaces may represent different types of network connections such as wireless and wired (physical) connections. Network interfaces 210 are shown separately from power supply 260, however it is appreciated that the interfaces that support PLC protocols may communicate through power supply 260 and/or may be an integral component coupled to power supply 260.

Memory 240 includes a plurality of storage locations that are addressable by processor 220 and network interfaces 210 for storing software programs and data structures associated with the embodiments described herein. In some embodiments, system 200 may have limited memory or no memory (e.g., no memory for storage other than for programs/processes operating on the system and associated caches).

Processor 220 comprises hardware elements or logic adapted to execute the software programs (e.g., instructions) and manipulate data structures 245. An operating system 242, portions of which are typically resident in memory 240 and executed by the processor, functionally organizes system 200 by, inter alia, invoking operations in support of software processes and/or services executing on the system. These software processes and/or services may include Electric Field Application processes/services 290 described herein. Note that while Electric Field Application processes/services 290 is illustrated in centralized memory 240, alternative embodiments provide for the process to be operated within the network interfaces 210, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the Electric Field Application processes/services 290 is shown as a standalone process, those skilled in the art will appreciate that this process may be executed as a routine or module within other processes.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system, comprising:
  a flexible scaffold defining a planar body formed by one or more layers, wherein the flexible scaffold includes a depth electrode port defined through the planar body of the flexible scaffold, the depth electrode port having one or more port contacts;
  a depth electrode having one or more terminal contacts being operable to assume a stimulating role or a measuring role and the one or more interfacing contacts establishing electrical communication between the one or more terminal contacts and the one or more port contacts of the depth electrode is positioned within the depth electrode port; and a control system in electrical communication with the one or more port contacts, the control system including a processor in communication with a memory, the memory comprising instructions, which, when executed, cause the processor to:
  apply a stimulating voltage to a target tissue area through the one or more port contacts in communication with the one or more terminal contacts;
  receive a measured voltage from the one or more terminal contacts through the one or more port; and
  optimize the stimulating voltage of based on the measured voltage,
  wherein the one or more port contacts and the one or more interfacing contacts facilitate electrical communication between the one or more terminal contacts of the depth electrode and the control system when the one or more interfacing contacts of the depth electrode are electrically coupled with the one or more port contacts of the depth electrode port; and
  wherein removal of the depth electrode from the depth electrode port electrically decouples the one or more terminal contacts from the control system.

2. The system of claim 1, further comprising:
one or more surface electrodes in electrical communication with the control system and positioned along the planar body of the flexible scaffold, wherein each surface electrode of the one or more surface electrodes comprises a surface contact that is operable to assume a stimulating role wherein the surface contact is configured to apply a stimulating voltage to the target tissue area when in contact with the target tissue area.

3. The system of claim 2, the surface contact being operable to assume a measuring tole, wherein the surface contact is configured to capture a measured voltage of the target tissue area when in contact with the target tissue area.

4. The system of claim 2, wherein the one or more surface electrodes are arranged along the planar body of the flexible scaffold in a grid pattern.

5. The system of claim 1, wherein the flexible scaffold includes one or more perforations that enable flexible conformity to a concave or convex surface.

6. The system of claim 1, wherein the depth electrode port defines a thru-hole configured for receipt of an associated depth electrode of the one or more electrodes.

7. The system of claim 1, wherein the one or more port contacts are exposed along an interior of the thru-hole of the depth electrode port.

8. The system of claim 1, wherein the one or more port contacts are in electrical communication with one or more port wires, the one or more port establishing electrical communication between the one or more port contacts and the control system and wherein the one or more port wires are encapsulated by the flexible scaffold.

9. The system of claim 1, wherein a port contact of the one or more port contacts is configured to communicate the stimulating voltage from the control system to the one or more terminal contacts of the depth electrode.

10. The system of claim 1, wherein a port contact of the one or more port contacts is configured to communicate the measured voltage from the one or more terminal contacts of the depth electrode to the control system.

11. The system of claim 1, wherein the depth electrode comprises:
an elongated electrode body defining a distal portion and an opposite proximal portion, wherein the distal portion includes the one or more terminal contacts and wherein the opposite proximal portion includes the one or more interfacing contacts.

12. The system of claim 11, wherein the depth electrode includes one or more tines protruding from the elongated electrode body.

13. The system of claim 12, wherein the one or more tines are configured to anchor the depth electrode within the target tissue area.

14. The system of claim 12, wherein the one or more tines are configured to contact the flexible scaffold to secure the depth electrode at a selected depth relative to the flexible scaffold.

15. The system of claim 12, wherein the one or more tines are operable for placement at various locations along the elongated electrode body of the depth electrode to enable placement of the depth electrode at variable depth relative to the flexible scaffold.

16. The system of claim 1, wherein the one or more terminal contacts being configured to apply the stimulating voltage to a target tissue area when assuming the stimulating role.

17. The system of claim 1, wherein the one or more terminal contacts being configured to measure the measured voltage from a target tissue when assuming the measuring role.

18. The system of claim 1, wherein the memory of the control system further includes instructions, which, when executed, cause the processor of the control system to:
  assign a stimulating role to the one or more terminal contacts of the flexible scaffold for application of the stimulating voltage to the one or more terminal contacts; and
  assign a measuring role to the one or more terminal contacts of the flexible scaffold for receipt of the measured voltage from the one or more terminal contacts.

19. The system of claim 1, wherein the memory of the control system further includes instructions, which, when executed, cause the processor of the control system to:
  identify one or more unconnected terminal contacts of the one or more terminal contacts.

20. The system of claim 1, wherein the memory of the control system further includes instructions, which, when executed, cause the processor of the control system to:
  assess the measured voltage received from the one or more terminal contacts with respect to a target voltage value; and
  adjust the stimulating voltage based on the assessment of the measured voltage with respect to the target voltage value.

21. A method, comprising:
coupling a modular electrode with a target tissue area, the modular electrode comprising:
  a flexible scaffold defining a planar body formed by one or more layers, wherein the flexible scaffold includes a depth electrode port defined through the planar body of the flexible scaffold, the depth electrode port having one or more port contacts; and
  a depth electrode having one or more terminal contacts and one or more interfacing contacts, the one or more terminal contacts being operable to assume a stimulating role or a measuring role and the one or more interfacing contacts establishing electrical communication between the one or more terminal contacts and the one or more port contacts of the depth electrode port when the depth electrode is positioned within the depth electrode port;

iteratively applying, by a control system in electrical communication with the one or more port contacts, a stimulating voltage to the target tissue area through one or more terminal contacts;

iteratively receiving, by the control system, a measured voltage from the one or more terminal contacts through one or more port contacts; and iteratively optimizing, by the control system, the stimulating voltage based on the measured voltage wherein the one or more port contacts and the one or more interfacing contacts facilitate electrical communication between the one or more terminal contacts of the depth electrode and the control system when the one or more interfacing contacts of the depth electrode are electrically coupled with the one or more port contacts of the depth electrode port; and wherein removal of the depth electrode from the depth electrode port electrically decouples the one or more terminal contacts from the control system.

22. The method of claim 21, further comprising:
modifying a shape of the modular electrode based on physiological need of the target tissue area.

23. The method of claim 22, wherein the step of modifying a shape of the modular electrode further comprises one or more of:
cutting the flexible scaffold to a desired shape or size; and
cutting a depth electrode to a desired shape or size.

24. The method of claim 21, further comprising:
inserting the depth electrode into the depth electrode port of the modular electrode to a desired depth.

25. The method of claim 21, further comprising:
assigning, by the control system, a stimulating role or a measuring role to a respective terminal contact of the one or more terminal contacts.

26. The method of claim 21, further comprising:
identifying, by the control system, one or more unconnected contacts of the modular electrode.

27. The method of claim 26, further comprising:
turning off, by the control system, one or more intentionally unconnected pins of the one or more unconnected contacts of the modular electrode.

* * * * *